United States Patent
Hlebovy et al.

(10) Patent No.: US 6,814,932 B2
(45) Date of Patent: Nov. 9, 2004

(54) DEVICE SUPPORT ACTIVATION SYSTEM

(75) Inventors: James C. Hlebovy, Chardon, OH (US);
Alan J. Greszler, Elyria, OH (US);
Nancy A. Robinson, Hudson, OH (US)

(73) Assignee: Steris Inc., Temecula, CA (US)

( * ) Notice: Subject to any disclaimer, the term of this patent is extended or adjusted under 35 U.S.C. 154(b) by 710 days.

(21) Appl. No.: 09/778,286

(22) Filed: Feb. 7, 2001

(65) Prior Publication Data

US 2002/0001537 A1 Jan. 3, 2002

Related U.S. Application Data

(60) Provisional application No. 60/193,521, filed on Mar. 31, 2000.

(51) Int. Cl.⁷ ................................................. A61L 2/18
(52) U.S. Cl. .......................... 422/28; 422/300; 134/32; 134/148; 134/201
(58) Field of Search ..................... 422/300, 28; 134/32, 134/33, 34, 148, 201

(56) References Cited

U.S. PATENT DOCUMENTS

| | | | |
|---|---|---|---|
| 4,281,674 A | 8/1981 | Tanaka et al. | |
| 4,548,197 A | 10/1985 | Kinoshita | |
| 4,731,222 A | 3/1988 | Kralovic et al. | |
| 5,090,433 A | 2/1992 | Kamaga | |
| 5,091,343 A | 2/1992 | Schneider et al. | |
| 5,225,160 A | 7/1993 | Sanford et al. | |
| 5,279,799 A | 1/1994 | Moser | |
| 5,405,587 A | 4/1995 | Fernandez et al. | |
| 5,552,115 A | 9/1996 | Malchesky | |
| 5,589,507 A | 12/1996 | Hall, II et al. | |
| 5,759,490 A | 6/1998 | Malchesky | |
| 6,013,227 A | 1/2000 | Lin et al. | |
| 6,047,431 A | 4/2000 | Canonica | |
| 6,068,815 A | 5/2000 | Oberleitner et al. | |

FOREIGN PATENT DOCUMENTS

WO  WO 00/18521  4/2000

*Primary Examiner*—Elizabeth McKane
(74) *Attorney, Agent, or Firm*—Fay, Sharpe, Fagan, Minnich & McKee, LLP

(57) ABSTRACT

A fluid delivery system (26) for an automated processor (A) delivers washing, microbial decontaminant, and rinse fluids to spray nozzles (102, 104, 106, 108, 110) in a chamber (12) for sequentially spraying the fluids over a lumened device (B), such as an endoscope. Sets of nozzles are operated in sequence to avoid the spray jets canceling each other out. The endoscope is supported on a rack (21) which is agitated by an activation system (330). This ensures ever changing points of contact between the device and the rack so that all external surfaces are contacted by the spray. A computer control system (80) controls cleaning, decontamination, rinsing, and drying stages of a cycle, and agitation of the rack at appropriate times, which are all carried out within the chamber, obviating the need for human contact with the device during processing.

20 Claims, 14 Drawing Sheets

DEVICE SUPPORT ACTIVATION SYSTEM

This application claims the priority of U.S. Provisional Application 60/193,521, filed Mar. 31, 2000.

BACKGROUND OF THE INVENTION

The present invention relates to the decontamination arts. It finds particular application in connection with an automated system for leak testing cleaning, sterilizing, and drying devices for medical, dental, mortuary, and pharmaceutical applications, and the like, and will be described with particular reference thereto. It should be appreciated, however, that the invention is also applicable to the decontamination of other devices in an automated processing system.

Medical devices, such as endoscopes, and other lumened instruments, are subjected to thorough cleaning and antimicrobial decontamination between each use. During medical procedures, the devices become coated with blood and other protein-rich body fluids. If the instruments are sterilized while they are coated with these materials, the high temperatures and/or chemicals used in the sterilization process tend to cause the materials to set as a hardened layer of biological residue that becomes difficult to remove. Not only do such residues present a barrier to sterilant penetration, but even when sterilized, they may later break down to form toxic substances which pose hazards to patients when the devices are reused.

Traditionally, such devices are often rinsed in a cleaning solution, such as an enzymatic cleaner, to remove the bulk of the blood and other body fluids from their surfaces. The rinsing process is generally carried out manually by immersing the devices in a shallow tray of the cleaning solution. However, for devices such as endoscopes, the cleaning fluid may not penetrate the length of the internal lumen, leaving a portion of the endoscope to become coated with dried body fluids. Additionally, the biological materials and strong cleaners may pose hazards to personnel coming into contact with them.

High temperature sterilization processes, such as steam sterilization in an autoclave, are generally unsuited to the sterilization of endoscopes because of the delicate components and materials from which they are manufactured. The high temperature and pressure tend to curtail the useful life of endoscopes, rubber and plastic devices, lenses, and portions of devices made of polymeric materials and the like. High temperature sterilization alone does not clean. Any body fluids that are not removed prior to thermal sterilization are typically baked on to the instrumentation.

Instruments which cannot withstand the pressure or temperature of the oven autoclave are often microbially decontaminated with gas, such as ethylene oxide gas or hydrogen peroxide vapor. Like steam, gases do not clean, requiring a separate cleaning operation. The ethylene oxide sterilization technique also has several drawbacks. First, the ethylene oxide sterilization cycle tends to be longer than the steam autoclave cycle. Second, some medical equipment can not be sterilized with ethylene oxide gas. Third, ethylene oxide is highly toxic and can present health risks to workers if not handled properly.

Liquid microbial decontamination systems are now utilized for equipment which can not withstand the high temperatures of steam sterilization. Peroxyacetic acid, or peracetic acid, is a useful sterilant and/or disinfectant for a variety of applications, including disinfection of waste and sterilization or disinfection of medical equipment, packaging containers, food processing equipment, and the like. It has a broad spectrum of activity against microorganisms, and is effective even at low temperatures. It poses few disposal problems because it decomposes to compounds which are readily degraded in sewage treatment plants.

In some situations, a technician mixes a disinfectant or sterilant composition with water and then manually immerses the items to be microbially decontaminated in the liquid composition. The high degree of manual labor introduces numerous uncontrolled and unreported variables into the process. There are quality assurance problems with technician errors in the mixing of sterilants, control of immersion times, rinsing of residue, exposure to the ambient atmosphere after the rinsing step, and the like. For sterilizing large, instruments, such as endoscopes with narrow lumens, however, a large receiving tray and a considerable quantity of decontaminant solution are used to accommodate and fully immerse the instruments.

Integrated decontamination systems, such as peracetic acid decontamination systems, have now been developed which provide a premeasured dose of a decontaminant in solution. Items to be sterilized are loaded into a receiving tray of a sterilization system and a cartridge of concentrated decontaminant inserted into a well. As water flows through the system, the decontaminant, which may be accompanied by surfactants and corrosion inhibitors, is diluted and carried to the receiving tray.

The items to be decontaminated are typically loaded into a treatment chamber through an opening closed by a door. It is desirable to maintain a seal between the door and the chamber, to prevent leakage of potentially hazardous sterilization chemicals from the chamber, and also to prevent ingress of potentially contaminated outside air into the chamber once the items are sterile.

Spraying the exterior of the instruments, while flowing decontaminant solution through the lumens, would have advantages over full immersion of the devices in reducing the quantity of decontaminant solution used. However, because of the complex shape of endoscopes, the spray jets may not reach all of the surfaces of the device. Additionally, interior surfaces of the lumened devices are not reached by the spray.

The present invention provides for a new and improved system and method for reprocessing endoscopes and the like, which overcomes the above-referenced problems and others.

SUMMARY OF THE INVENTION

In accordance with one aspect of the present invention, a system for microbially decontaminating a device is provided. The system includes a cabinet which defines an interior chamber for receiving the device. Spray nozzles, disposed within the chamber, spray a decontaminant fluid over an external surface of the device. A support supports the device within the chamber. An activation system displaces at least a portion of the support for changing points of contact between the device and the support.

In accordance with another aspect of the present invention, a system for cleaning and microbially decontaminating endoscopes is provided. The system includes a cabinet defining a vertically elongated chamber having rear and side walls and a front door. Spray nozzles are mounted on at least the rear and side walls of the chamber for spraying liquid cleaning and microbially decontaminating solutions. A hanger is on the chamber rear wall. A rack is configured to support a coiled endoscope. The rack is pivotally and removably hung on the hanger. A reciprocating drive having a drive member extends from the chamber rear wall adjacent the rack such that as the drive member reciprocates it engages and pushes the rack to pivot on the hanger and disengages from the rack to permit the liquid cleaning and decontaminating solutions to contact engaging surfaces of the rack and the drive member.

In accordance with another aspect of the present invention, a method of microbially decontaminating a device is provided. The method includes mounting the device on a support, spraying a microbial decontaminant solution over the device to microbially decontaminate the exterior surfaces of the device, and agitating the support to change points of contact between the device and the support.

One advantage of one embodiment of the present invention is that an endoscope or other lumened device is cleaned and microbially decontaminated in a single automated process.

Another advantage of one embodiment of the present invention is that hazards posed to personnel by handling contaminated devices are minimized.

A yet further advantage of one embodiment of the present invention is that a decontaminant delivery system ensures decontamination of all exterior and interior surfaces of the device being decontaminated.

Another advantage of one embodiment of the present invention is that spraying, rather than fully immersing large items, such as endoscopes, reduces the quantities of water and decontaminant, pretreatment agents, and cleaning agents used.

A further advantage of the present invention is that it prevents seals from forming at the point of contact between the endoscope or other lumened device and the support members of the holding rack.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
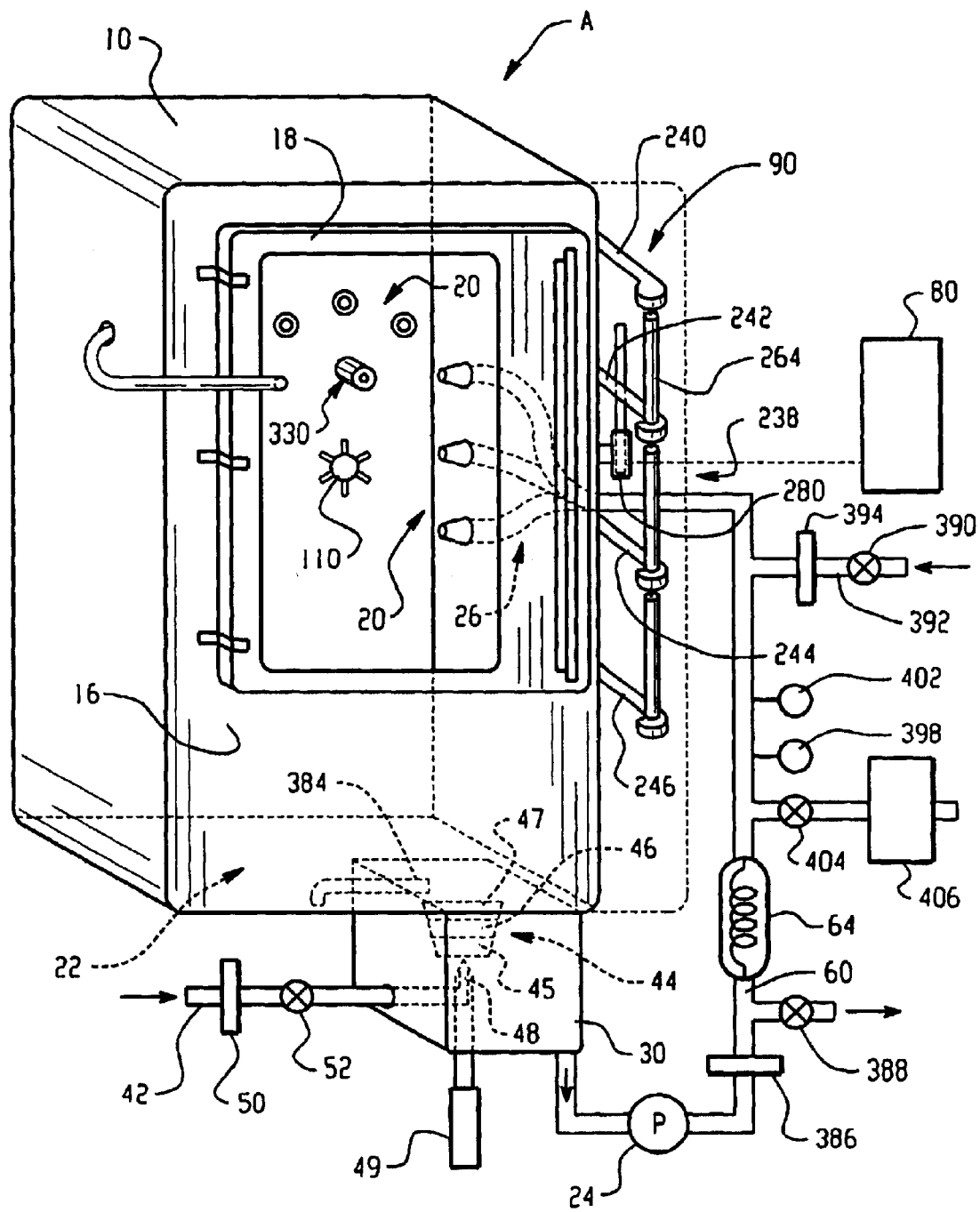
FIG. 1 is a perspective and diagrammatic view of a cleaning and antimicrobial decontamination processor according to the present invention.
Figure 2:
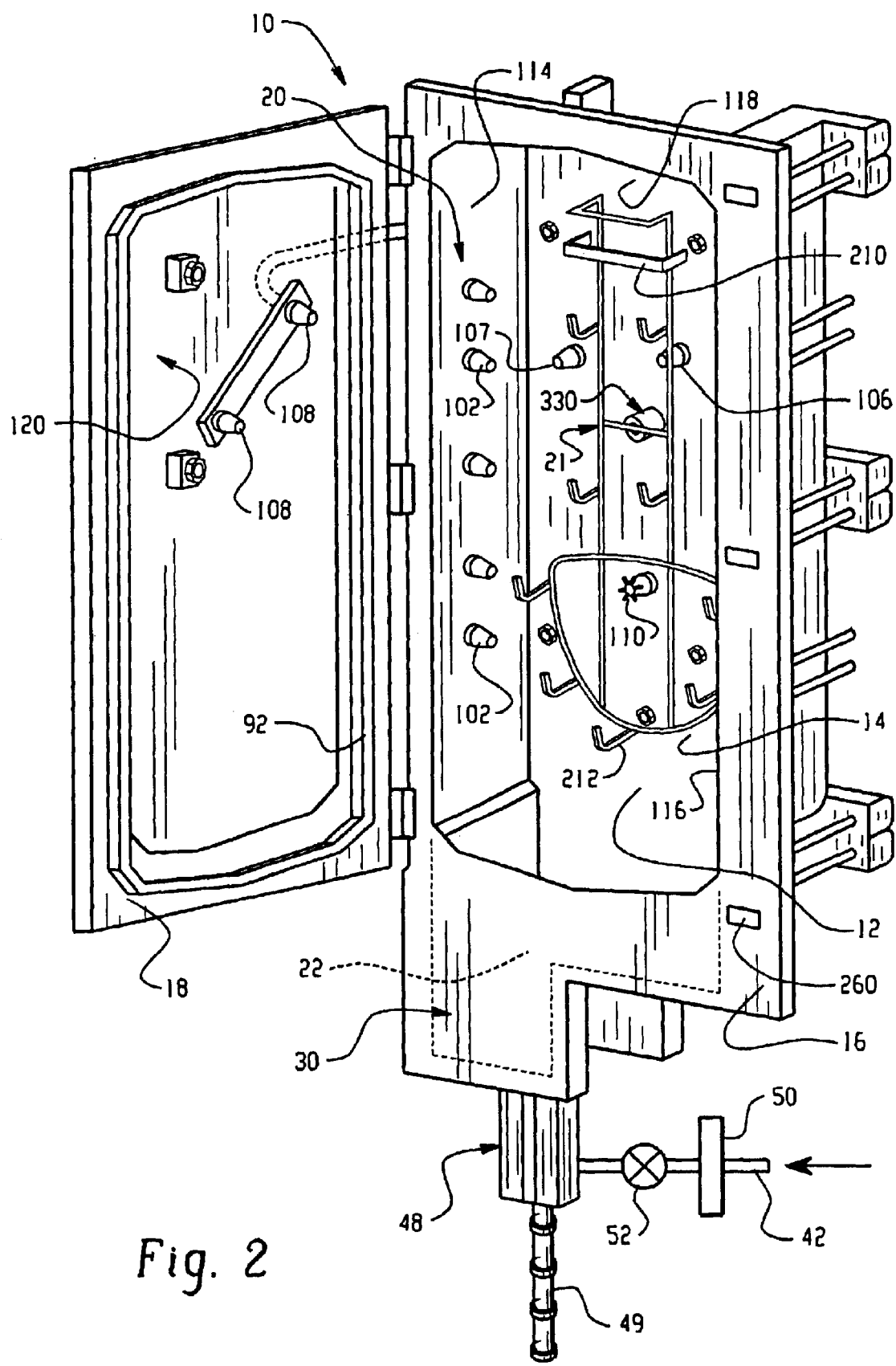
FIG. 2 is a perspective view of the chamber of FIG. 1 with the door open.

With reference to FIGS. 1 and 2, an automated liquid cleaning and antimicrobial decontamination processor or system A sequentially leak tests and washes then sterilizes or disinfects items, such as medical, dental, and pharmaceutical devices, and the like. While particular reference is made to the cleaning and microbial decontamination of lumened instruments, such as endoscopes, it is to be appreciated that the processor A has application in the cleaning and/or decontamination of a variety of different devices. The processor A is particularly suited to the cleaning and microbial decontamination of instruments which are heat labile, i.e., those which, because of their components or materials, may be damaged by temperatures over about 60° C.

The term "endoscope," as used herein, should be understood to include a wide variety of lumened instruments, including angioscopes, artheroscopes, laparoscopes, bronchoscopes, duodenoscopes, catheters, and the like.

The term "microbial decontamination" and other terms relating to decontaminating will be used herein to describe sterilization, disinfection, and other antimicrobial treatments which are designed to destroy microorganisms contaminating the items. The term "washing" will be used herein to describe the physical removal of soil from the items, without necessarily destroying the microorganisms contaminating the items.

The processor A includes at least one combined washing and microbial decontamination cabinet 10 which defines an interior washing and microbial decontamination chamber 12.

Items to be washed and microbially decontaminated are loaded into the chamber 12 through an opening 14 in a vertical front wall 16 of the cabinet, closed by a door 18. Within the chamber, a fluid delivery system 20, comprising spray jets and connection nozzles, sprays a washing/decontaminant solution over exterior surfaces of the items and directs the solution through internal passages of endoscopes and other objects with lumens. A rack 21 supports one or more endoscopes in a suitable position for optimal effective washing and decontamination by the spray system 20. The endoscope may be loaded on to the rack prior to loading into the chamber, or the rack may be positioned in the chamber prior to attachment of the endoscope.

A collection tank or sump 22 forms the base of the cabinet 10 and receives the sprayed washing/decontaminant solution as it drips off the items. A high pressure pump 24 delivers the washing/decontaminant solution under pressure to the spray system 20 through a fluid distribution system or manifold 26.

A well or mixing chamber 30 sequentially receives doses of a cleaner concentrate and a concentrated decontaminant. The cleaner concentrate mixes with water to form a washing solution for cleaning the items prior to antimicrobial decontamination. The concentrated decontaminant is preferably an antimicrobial agent or comprises reagents which react to form an antimicrobial agent on mixing with water. The cleaner concentrate may be an enzymatic cleaner, or an acid or alkaline cleaner, and may include detergents, surfactants, and the like. A preferred cleaner concentrate is a pH neutral, low foaming composition, which is not harmful to the components of the device. The cleaner concentrate and concentrated decontaminant may be in solid or in liquid form. As shown in FIGS. 1 and 2, the well 30 is integral with the collection tank 22 of the chamber, although a separate well is also contemplated.

A preferred antimicrobial agent is peracetic acid, either in concentrated liquid form, or as a reaction product of powdered reagents, such as acetyl salicylic acid and sodium perborate. Other peracids, or mixtures of peracids, are also useful antimicrobial agents. A water inlet 42 supplies water, typically from a municipal water system, to the well 30. The water mixes with detergents, surfactants, corrosion inhibitors, pH buffers, the concentrated decontaminant, and other selected components in the well to form wash, decontaminant, or other solutions.

Preferably, the concentrated decontaminant, cleaner concentrate, and the corrosion inhibitors, buffers, and other components are supplied in a disposable package or cup 44 which is positioned in the well 30 prior to a decontamination cycle. The cup 44 separately holds the measured doses of the cleaner concentrate, a pretreatment mixture of buffers, surfactants, corrosion inhibitors, and other pretreatment chemicals, and the concentrated decontaminant in separate compartments 45, 46, and 47, respectively, for separate release into the system. In this way, the items are first washed and then microbially decontaminated. A cup cutter 48, or other suitable opening member, driven by an drive system, such as an air cylinder 49 is positioned at the base of the well 30 for opening selected compartments of the cup.

The quantity of water entering the system is regulated to provide a washing/decontaminant solution of a desired concentration in the decontamination chamber 12. The water is preferably passed through a 5 micron filter 50 in the water inlet line 42, which filters out particulates. Optionally, a 0.1 micron filter may be provided to remove microbes. A valve 52 in the water inlet 42 closes when the selected quantity of water has been admitted.

Figure 3A:
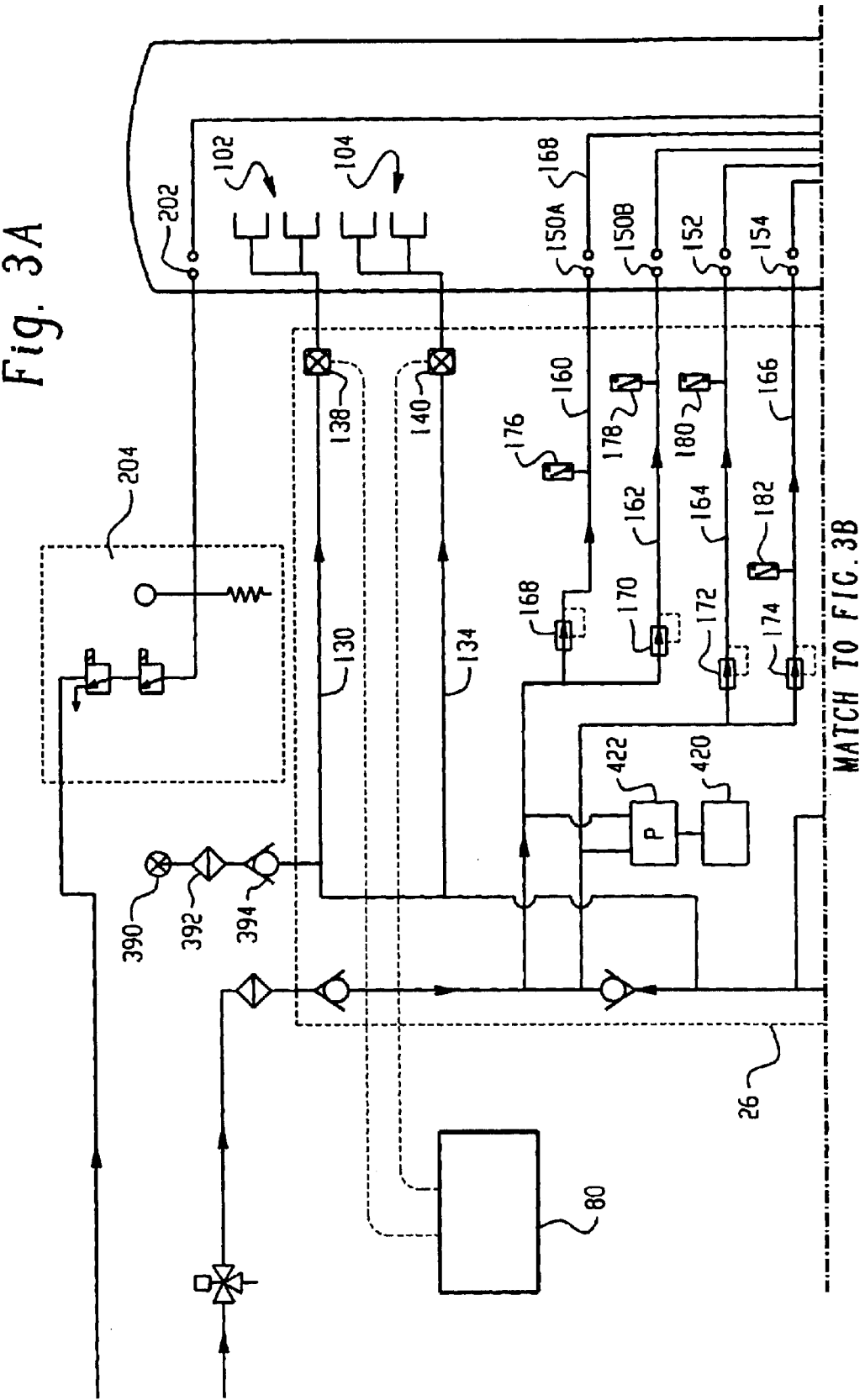
FIGS. 3A and 3B is a plumbing diagram of the system of FIG. 1.
Figure 3B:
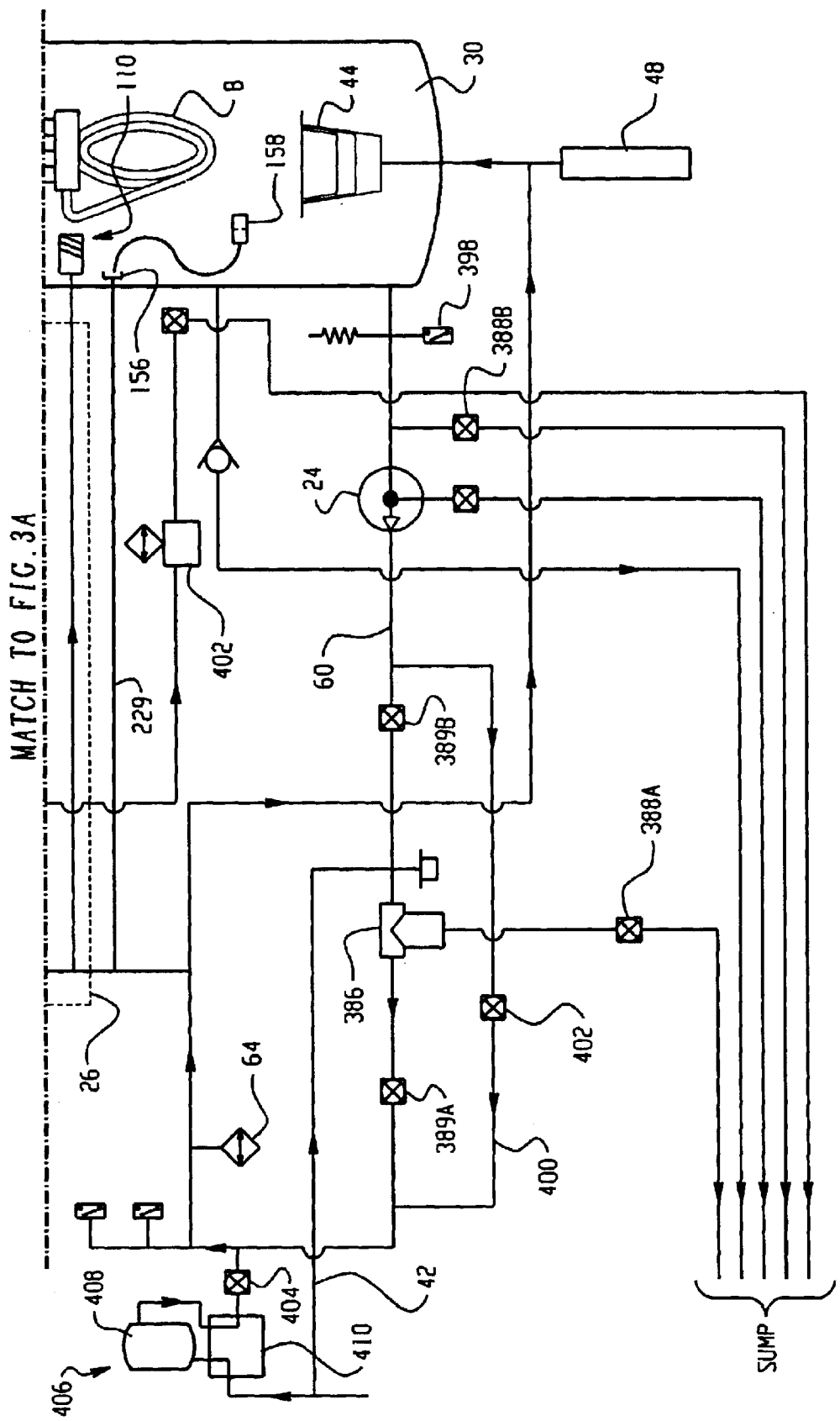

With reference also to FIG. 3, a fluid supply pathway 60 connects the well 30, the pump 24, and the fluid distribution system 26. Thus, a fluid circulation loop is provided which circulates the washing and decontaminant solutions through the well 30, pathway 60, fluid distribution system 26, and spray system 20. Sprayed solutions collect in the well and are pumped by the pump 22 through the pathway, fluid distribution system, and back to the spray system 20. A heater 64, situated in the fluid supply pathway 60, heats the decontaminant solution and optionally the washing solution and a rinse liquid to a preferred temperature(s) for effective cleaning, decontamination, and rinsing.

A computer control system 80 controls the operation of the processor A, including the pump 24, the heater 64, the valves 52, locking of the door 18, and the like. The control system 80 may control one or more additional systems A, if desired.

A door latching and locking mechanism 90 holds the door in the closed position against the front face of the cabinet and prevents the opening of the door during a washing and decontamination cycle. A seal member 92, such as a gasket, is positioned between the door and the front face 16 of the cabinet to provide a fluid tight seal at the pressures used in the cabinet.

Figure 4:
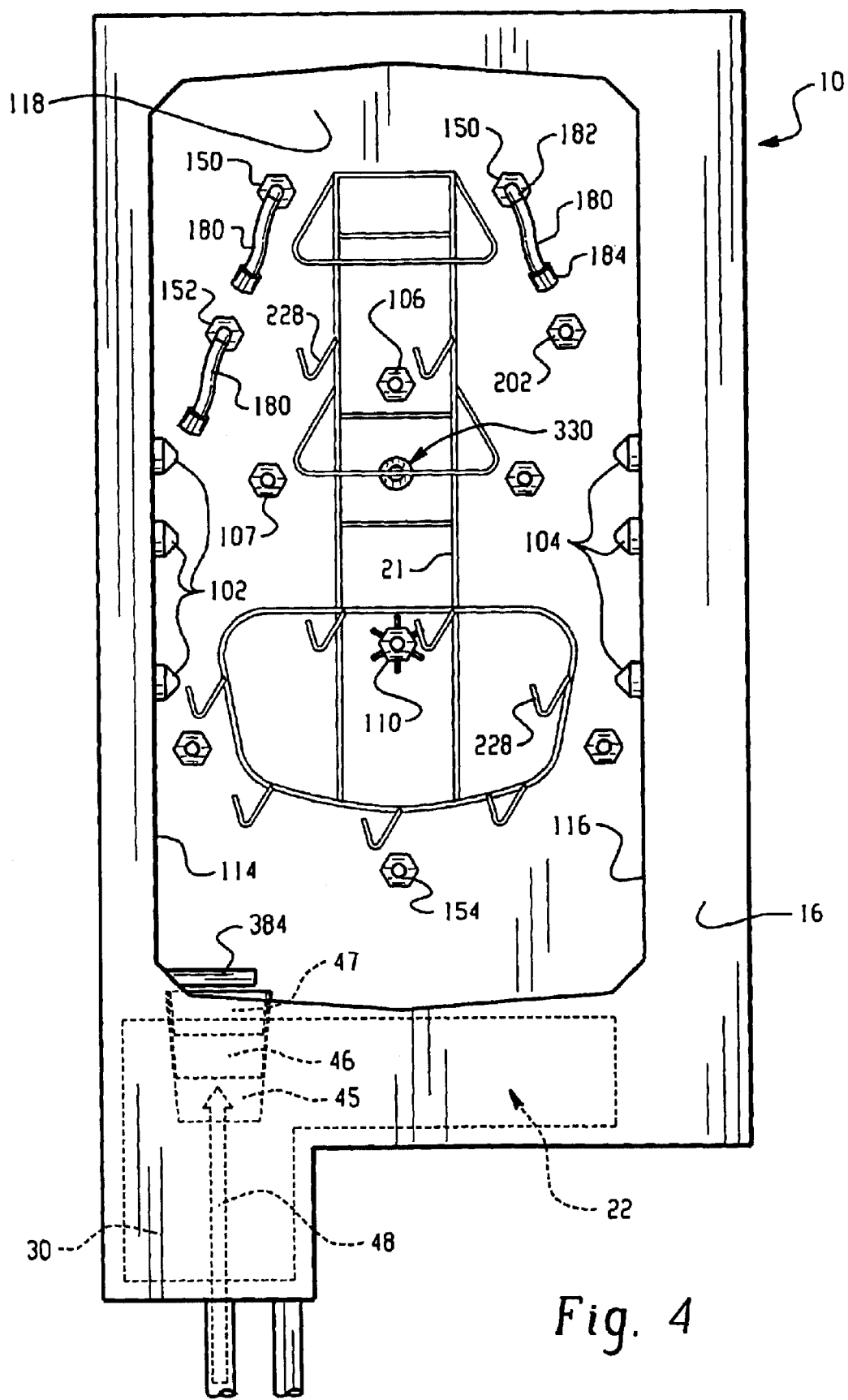
FIG. 4 is a front view of the chamber of FIG. 2.

With reference to FIGS. 2 and 3, and also to FIG. 4, the spray system 20 includes several types of spray nozzles 102, 104, 106, 107, 108, and 110, which direct the cleaning/decontaminant solutions over an endoscope B and other items within the chamber 12 for complete coverage. The pump supplies the nozzles with the washing/decontaminant fluid at a pressure of about 60–80 psi (4.2–5.6 Kg/sq.cm). The spray nozzles 102 and 104 are located on left and right side walls 114, 116 of the chamber 12, respectively. These have a spray angle of preferably about 90°, for impacting the surfaces of the endoscope at high pressure. The spray nozzles 106 are located on a rear wall 118 of the chamber. These nozzles spray over a wider angle, preferably about 120 degrees, for wider coverage, although with lesser impact than the nozzles 102, 104. The spray nozzle 107 extends forward from the rear wall. It has a narrow spray angle of 45 degrees and is aimed to directly impact a contact point on the device. The spray nozzles 108 are attached to an inner surface 120 of the chamber door 18.

The spray nozzle 110 extends forwardly from the rear wall 118 of the chamber and directs cleaning fluid radially in multiple directions for wide coverage. As shown in FIG. 4, the nozzle 110 includes multiple spray heads. Six spray heads are shown, angled at 60 degrees apart, for a 360 coverage. Alternatively, spray nozzle 110 is a rotating nozzle, which is rotated through a 360 degree path to deliver solution in many directions.

Figure 5:
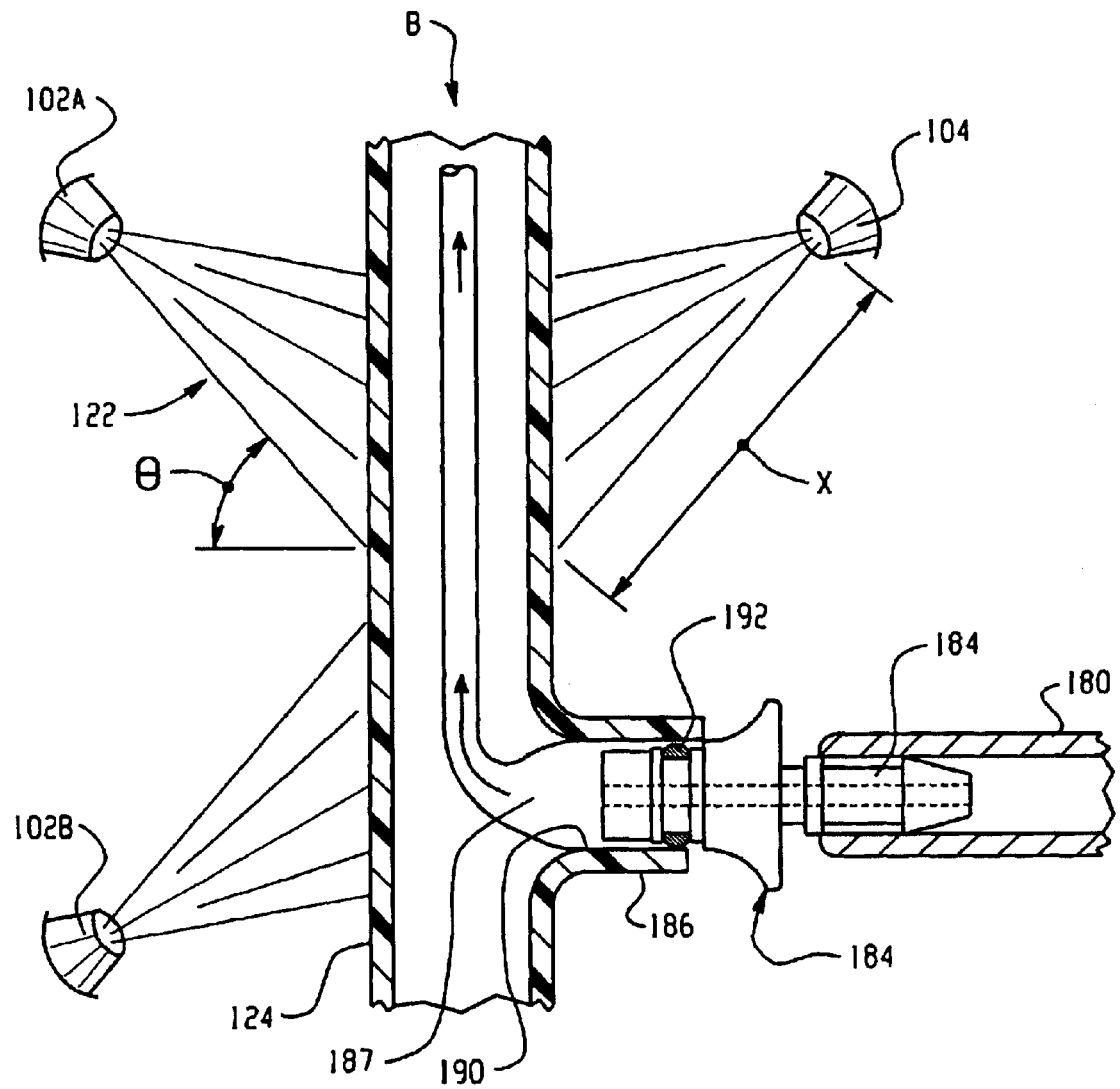
FIG. 5 is a sectional view of a section of an endoscope showing spray jets impinging on its outer surface.

With reference also to FIG. 5, the spray nozzles 102, 104, 106, 108 are angled such that all surfaces of the endoscope B are contacted by the spray of decontaminant solution emitted from the nozzles. Specifically, each nozzle spray jet 122 strikes the endoscope surface 124 at a shallow angle $\theta$, relative to normal to the endoscope surface. Preferably, the angle $\theta$ is less than about 45 degrees, i.e., each surface of the endoscope is struck with at least one spray jet at an angle of no more than about 45 degrees from normal. Thus, the nozzles are angled to deliver the decontaminant/cleaning solutions at different angles. For example, as shown in FIG. 5, nozzle 102A is directed downwardly, while nozzle 102B is directed upwardly.

Additionally, each surface of the endoscope is no more than a maximum distance x from the closest spray nozzle, so that the endoscope receives the full force of the spray jet. Preferably, x is no more than 20 centimeters, more preferably, x is less than about 15 centimeters. Further, each surface of the endoscope is no less than a minimum distance from the closest spray nozzle, so that the endoscope receives the full force of the spray jet. Preferably, the minimum distance is at least 5 centimeters.

With reference once more to FIG. 3, to obtain these minimum criteria, the nozzles are in many cases positioned so closely that their sprays may interact. The interaction, prior to contacting the instrument, can negate or alter their force, angle of impact and other characteristics. To avoid the spray jets 122 from different directions canceling each other out, the jets are pulsed in sequence. For example, the manifold 26 includes a first fluid line 130 which supplies nozzles 102 and a second fluid line 134 which supplies nozzles 104. The controller 80 sequentially opens an air diaphragm valve 138 in the first line 130 for a few seconds, allowing the cleaning/decontaminant and rinse solutions to flow to nozzles 102, then closes valve 138 and opens an air diaphragm valve 140 in the second line 134 for a few seconds, allowing the cleaning/decontaminant solution to flow to nozzles 104.

With reference now to FIGS. 2 and 3, the spray system 20, in addition to the nozzles, also includes several connection ports 150, 152, and 154, for supplying washing/decontaminant solution to the internal passages of the endoscope B and an associated set of biopsy forceps. An additional port 156 may be provided for supplying the solutions to a valve reprocessor 158. The different internal passages of a typical endoscope and biopsy forceps are rated to withstand different maximum pressures. The connection ports supply washing/decontaminant solution at an appropriate pressure that is below the maximum pressure rating for the passage to which the connection port supplies solution. For example, as shown in FIG. 3, the manifold includes fluid lines 160, 162, which supply fluids to connection ports 150A and 150B at a first pressure, preferably of no more than about 1.4 Kg/sq.cm, for washing/decontaminating the lumens, and line 164, which supplies connection port 152 at a second pressure, preferably of no more than about 210 mmHg (2.8 Kg/sq.cm), for washing/decontaminating elevated guide wire passages. Another fluid line 166 supplies connection port 154 at a third pressure, preferably of no more than about 210 mmHg (2.8 Kg/sq.cm), for cleaning/decontaminating the biopsy forceps. Pressure regulators 168, 170, 172, and 174 in each of the fluid lines 160, 162, 164, and 166 are set to ensure that the maximum pressure is not exceeded. Pressure switches 176, 178, 180, 182 detect the presence of a pressure drop in the lines 160, 162, 164, and 166.

With reference once more to FIGS. 4 and 5, the connection ports 150, 152, and 154 are connected with the respective internal passages of the endoscope and biopsy forceps by tubes 180, each with a quick connect 182 at the connection port end and a suitable connector 184 at the other end for connecting with the inlet port 186 of the respective internal passage, for releasably and quickly connecting the fluid lines with the respective internal passages 187. To avoid confusion and accidental over-pressurization of the various lumens 187, the quick connects 182 for the low pressure lines 160, 162, 166 will not connect with the high pressure connection port 152. In the preferred embodiment, the connectors 182 have different sizing; but, different shapes and the like are also contemplated.

The connectors 184 are preferably leaking connectors, i.e., they allow a controlled portion of the washing/decontaminant solution to flow between the connector and the inlet port to contact all adjacent surfaces 190 of the inlet port 186. This ensures that all the accessible surfaces of the internal passage 187 are contacted with the washing/decontaminant solution. The relative flow is balanced for optimum cleaning of all points. The majority of the solution travels along the full length of the endoscope internal passage and out of the endoscope into the chamber 12.

In the embodiment of FIG. 5, the leaking connector 184 includes a metal C-ring 192. The C-ring is seated loosely in an annular groove in a portion of the connector which is received past a small lip of the inlet port 186. The ring spaces the connector from the internal surfaces 190 of the inlet port, allowing a portion of the fluid to flow around it and out of the inlet port 186. Other configurations of male and female leaking connectors are also contemplated. Analogous plug members with controlled leakage at the interconnection are used to plug selected ports.

With reference to FIG. 3, a further connection port 202 in the chamber connects a leak detector 204 with the venting connector port of the endoscope for testing the endoscope for leaks. The leak detector supplies air under pressure to the venting connector port and its associated internal passage for detecting leaks from the internal passage. If leaks are found, the leak detector aborts the cycle to prevent fluids from leaking into sensitive regions of the scope.

Figure 6:
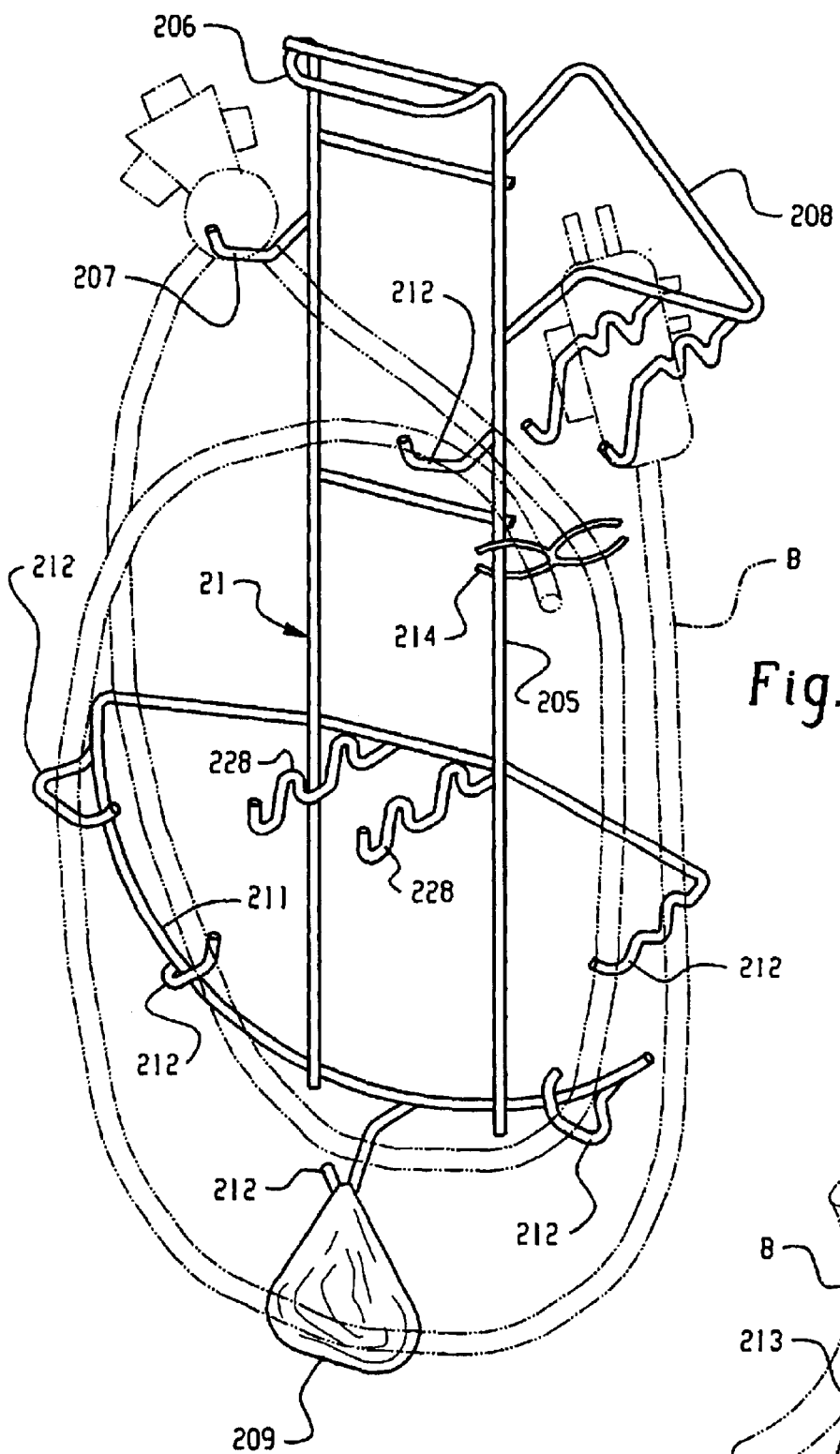
FIG. 6 is a perspective view of the endoscope rack of FIGS. 2 and 4 with an endoscope shown in phantom.

With reference once more to FIG. 2 and reference also to FIG. 6, the rack 21 is preferably removable from the chamber 12. To accommodate different types of endoscopes, several racks 21 are provided, each one configured for receiving a particular type or family of endoscopes. The appropriate rack is selected according to the endoscope to be reprocessed, and the endoscope fitted to the rack prior to or after hooking or otherwise attaching the rack within the chamber. The rack includes a central rectangular support frame 205 with a carrying and connecting handle 206 attached at an upper end thereof. Mounted on the frame are support members 207, 208, which are configured for receiving the endoscope operating section and light guide connector sections, respectively. Small, separate components of the endoscope, such as hoods, plugs, and other semi-reusable items, may be hung from the rack in a porous bag 209. The upper end of the rack is releasably mounted on a suitably receiving member or members 210 within the chamber.

The rack includes an arcuate portion 211 which supports a number of pegs or tabs 212. The pegs on the arcuate section and the support frame 205 define a circle for support of the flexible tubes (the umbilical cable and the insertion tube) of endoscope B such that the tubes curve in a wide loop on the rack 21. Preferably, the rack and hooks position the endoscope such that it is not bent sharper than its minimum bend radius, typically about 15 centimeters. In the preferred embodiment, the bend radius is at least 18 centimeters, i.e., no portion of the flexible portions of the endoscope tubes are bent into a curve which has a radius of less than about 18 cm. This ensures that as the endoscope is wrapped around the pegs 212 it is correctly positioned for receiving the full force of the spray jets and that there are no inaccessible or potentially damaging tight bends in the endoscope. Depending on the stiffness of the flexible tube, the tube is mounted inside and/or over the pegs. The pegs are positioned at angular intervals such that the end of the tube of every endoscope in the family ends up near, but just beyond, one of the pegs.

The rack is preferably formed from stainless steel or other materials which are resistant to the decontaminant solution and other chemicals employed in the chamber.

Figure 7:
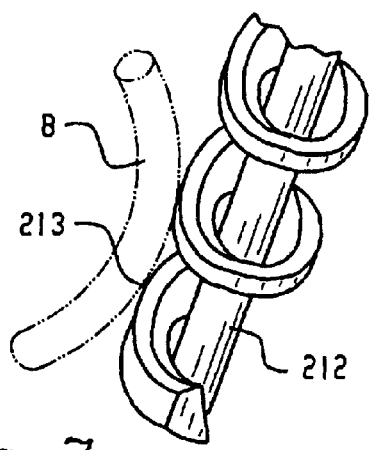
FIG. 7 is an enlarged perspective view in partial section of a rack peg of FIG. 6.

To minimize contact with the endoscope, and improve access of the spray of washing or decontaminant solutions to the contact areas, the support members 207, 208, and pegs 212, preferably make only "point contact" with the endoscope, i.e., the area of contact is as small as is possible, without resulting in damage to the endoscope. In one preferred embodiment, the pegs and support members are formed from a screw-threaded stock, which contacts the endoscope only at tips 213 of the threads, as shown in FIG. 7. Preferably, the tips of the threads are blunted, such as acme threads or threads with a sinusoidal or other curved cross section, to avoid indentation, scratching, or other damage to the endoscope. A clip 214 clips to the rack and provides a loosely constraint to the endoscope tip.

The rack is preferably formed from stainless steel, or formed from other materials, which are resistant to the decontaminant solution and other chemicals employed in the chamber.

Figure 8:
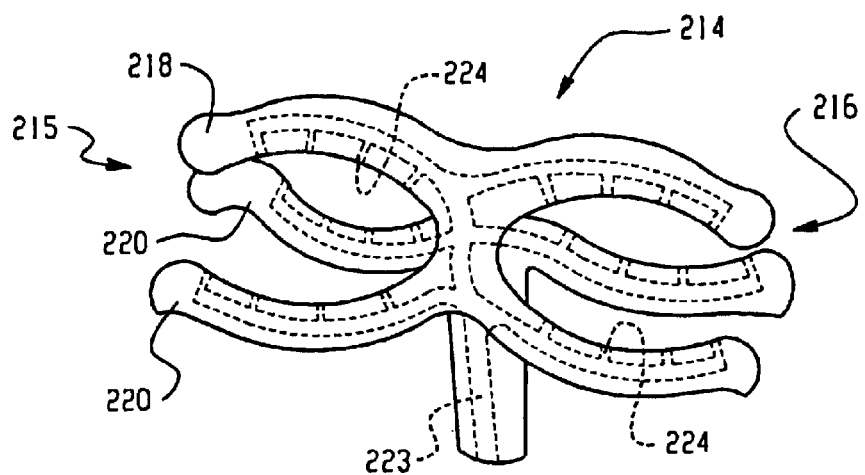
FIG. 8 is a perspective view of one embodiment of an endoscope clip.
Figure 9:
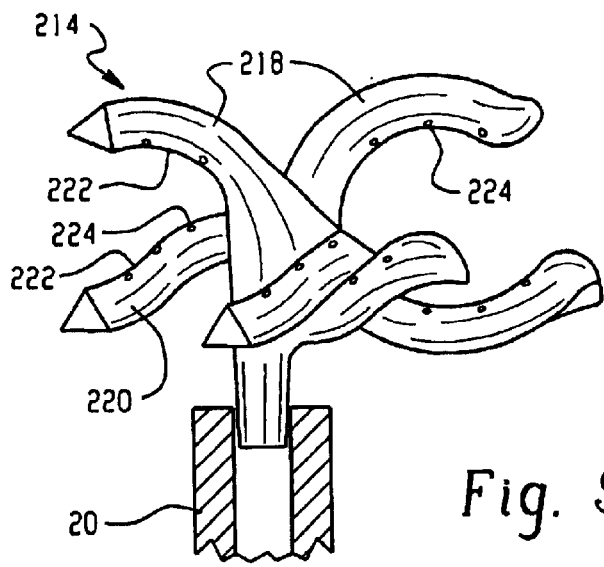
FIG. 9 is a perspective view of the endoscope clip of FIG. 8 showing the fingers in partial section.
Figure 10:
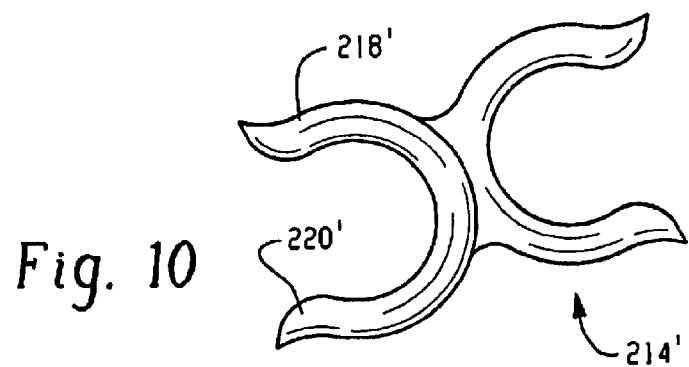
FIG. 10 is a perspective view of another embodiment of an endoscope clip.
Figure 11:
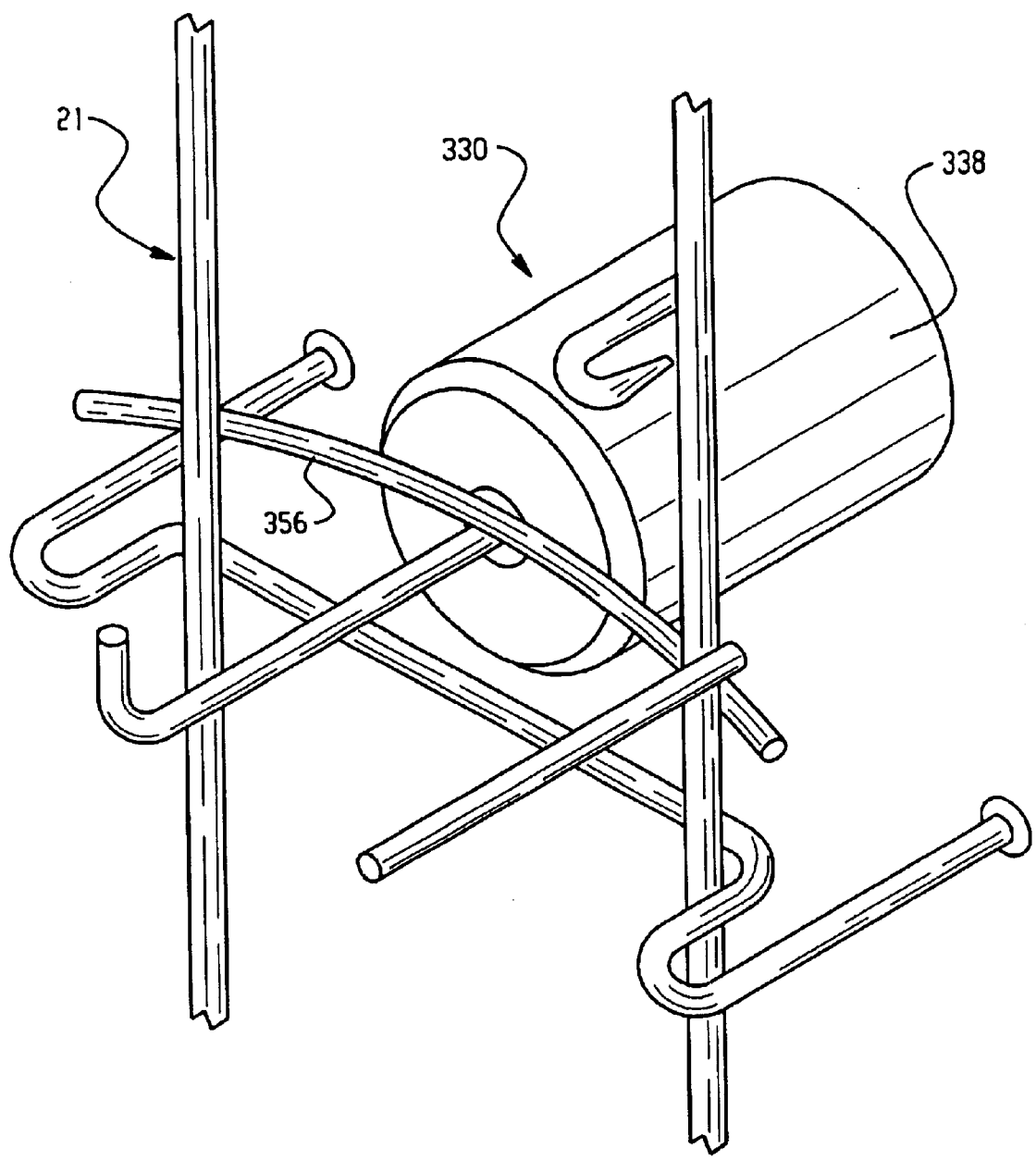
FIG. 11 is an enlarged perspective view of the cylinder and piston of the moveable rack activation system of FIG. 1.

With reference also to FIGS. 8 and 9, one or more clips 214 is attached to the tip of the endoscope insertion tube, or other flexible, tubular portion of the endoscope, to prevent it swaying and breaking during transport or during the cycle. The clip includes a first gripping portion 215, which releasably grips the tip of a flexible portion of the endoscope B and a second gripping portion 216, which releasably grips another portion of the endoscope or the rack 19. Each of the gripping portions includes at least one upper finger 218 and at least one lower finger 220. The clip 214 of FIGS. 8 and 9 includes one upper finger and two, spaced lower fingers. FIG. 10 shows an alternative embodiment of a clip 214', where each gripping portion includes one upper finger 218' and one lower finger 220'. Other embodiments of the clip are also contemplated. For example, the clip could be permanently attached to the rack 21 and have only a single gripping portion for gripping the endoscope tip.

The clip 214, 214' is preferably formed from a resiliently flexible material, such as Nylon or Delrin™. Accordingly, when the tubular portion to be gripped (e.g., the endoscope tip or rack) is pressed against the tips of the fingers 218, 220, the upper and lower fingers are splayed apart, allowing the tubular portion to be inserted therebetween. The fingers 218, 220 then snap back to grip the tubular portion firmly, but not so tightly that access of the washing and decontaminant solutions is prevented. The material selected for forming the clip is also one which is resistant to the chemicals used in the washing and microbial decontamination system.

With particular reference to FIG. 8, it is important to minimize the contact area between the clip 214, 214' and the endoscope tip to ensure complete sterilization of the outer surfaces of the endoscope. To achieve this, the fingers 218 and 220 have a triangular cross section with a ridge 222 of the triangle, of very small radius, in contact with the endoscope (essentially point contact). This reduces shadowing, i.e., the interference of the clip with the spray jets. Additionally, providing two, spaced apart lower fingers 220 allows the solutions to contact the endoscope tip between the fingers while maintaining a firm grip on the tip. To avoid damage to the endoscope, the contacting ridge 222 is slightly rounded rather than defining a sharp point. The shape of the ridge is optimized to minimize contact while avoiding damage or indentations in the tip.

Optionally, the clip 214 is fluidly connected with the fluid distribution system 26. A fluid pathway 223 inside the clip selectively connects the fluid distribution system with apertures 224 defined in the ridges 222. The washing and decontamination fluids flow out of the apertures 224 and over the surfaces of the endoscope in contact with the clip which otherwise may escape the full force of the spray jets from the nozzles.

Preferably, several interchangeable clips 214 of different dimensions are provided so that an appropriate clip may be selected according to the dimensions of the endoscope/tip.

Optionally, the rack 21 includes support members 228, for supporting coiled biopsy forceps, which are designed to pass through a channel of the endoscope, or other accessories to be cleaned and decontaminated. To anchor the forceps more securely, they are preferably coiled on a carrier which is supported on pegs 228.

The rack 21 and clip(s) 214 are designed to hold the endoscope firmly to avoid damage, but yet allow a small amount of movement (i.e., wobbling) of the endoscope during processing, facilitated by the pulsing of the spray jets. This movement allows access of the solutions to those areas of the endoscope making contact with the rack pegs, support members and clips to ensure that the entire exterior surface of the endoscope is thoroughly cleaned and microbially decontaminated.

With reference now to FIGS. 1 and 11–14, the endoscope rack is agitated, throughout at least the sterilization portion of the cycle, by a support activation system 330. The activation system is mounted such that it contacts the rack and provides a pulsing movement which causes the rack to vibrate or move, shaking the endoscope slightly in the process. In this way, the position of the endoscope changes frequently and the positions of the contact points also change.

Figure 12:
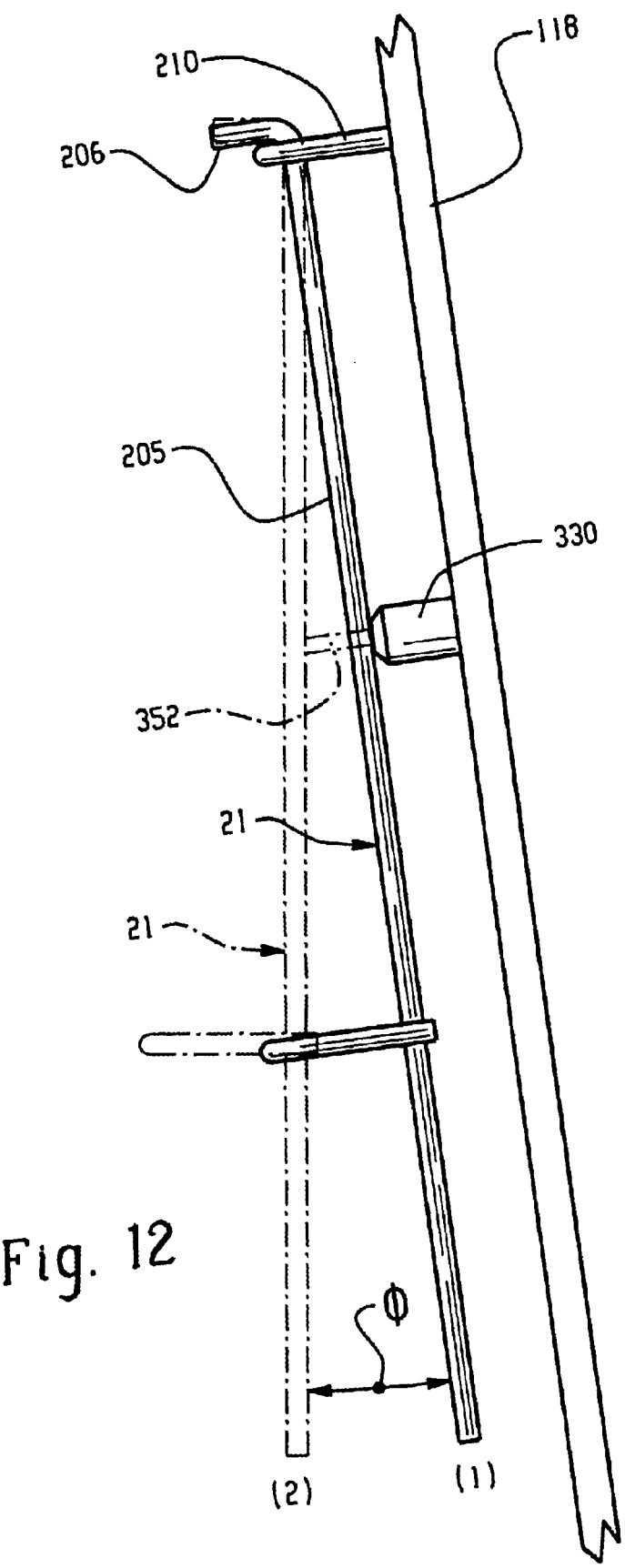
FIG. 12 is a side view showing the positions of the rack of FIG. 11 before and after (phantom) actuation of the piston.
Figure 13:
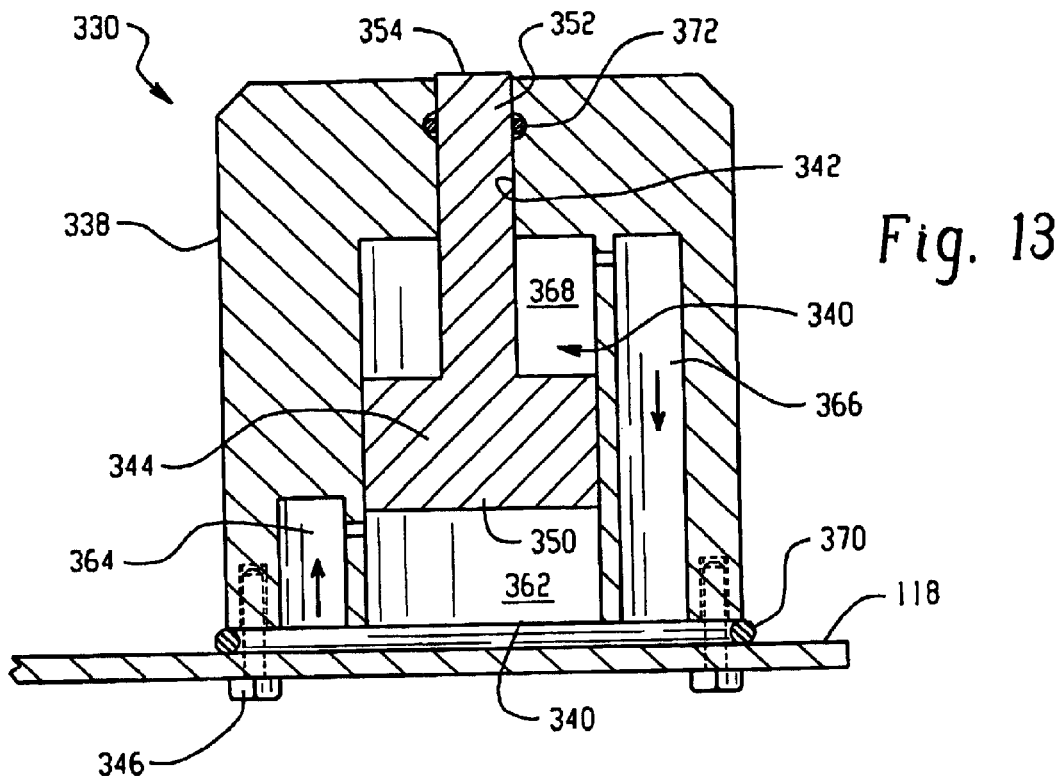
FIG. 13 is an enlarged side view showing the activation system prior to activation and/or after deactivation.
Figure 14:
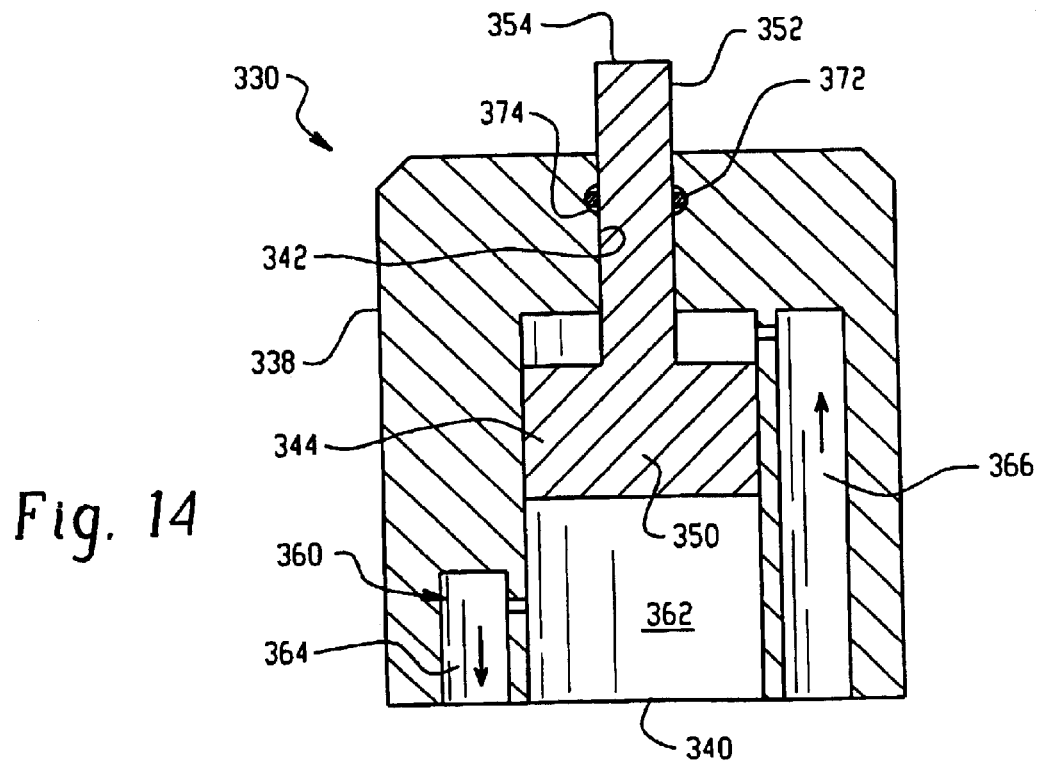
FIG. 14 is an enlarged side view showing the activation system after activation.

The system 330 includes a housing or cylinder 338, which defines an internal cavity 340 having an opening or bore 342 in a forward end thereof. A piston 344 is received by the housing. The housing is affixed adjacent a rearward, open end 344 to the rear wall of the chamber 12 by screws 346 or other suitable fixing members. The piston 344 includes a cylindrical portion 350, which reciprocates within the cavity, and is shaped for sliding engagement with the walls of the cavity. A shaft 352 extends forwardly of the cylindrical portion such that its tip 354 protrudes through the opening 342 when the cylindrical portion is in the position shown in FIG. 14. The piston shaft 352 is preferably in general alignment with a solid portion, e.g. a horizontal support bar 356, of the rack. As shown in FIG. 12, the point of contact with the rack is spaced from the top of the rack so that the rack pivots around the hooks 210 when the contact point is displaced.

When the rack 21 is stationary, it hangs in a vertical, or substantially vertical, position within the chamber (FIG. 12, solid lines). When the piston is driven forward to the position shown in FIG. 14, the piston shaft contacts or strikes the support 356. Upon striking the support bar 356, the rack is displaced from its vertical position and pivoted at an angle φ away from vertical to an angled position, (FIG. 12, hatched lines). The displacement angle φ is dependent on the force with which piston 344 strikes the rack. When the piston is returned to the position shown in FIG. 13, the rack falls back to its original position and, depending on the force used and speed of extending and retracting the piston, may bounce one or more times on the cylinder before settling back to rest.

Preferably, the piston shaft 352 is forced out of the cylinder with a force sufficient to displace the rack from its resting vertical position and, most preferably, cause the rack to vibrate. The force of the piston should not be excessive such that the any portion of the endoscope becomes permanently dislodged from the rack. Displacement of the rack from its resting vertical position changes the angular position of the rack and the endoscope with respect to the spray jet nozzles, allowing the endoscope to be exposed to different spray contact angles. Vibrating preferably changes the position of the endoscope on the support pegs or any other support member of the rack. Specifically, vibrating the rack results in a change of the position of the endoscope. Changing the position of the endoscope on the support pegs changes the contact site, i.e., the portion of the endoscope making direct contact with the support peg or other portion of the rack. Therefore, upon movement and vibration of the rack, new surface areas of the endoscope are exposed to the spray nozzles, such that all of the endoscope is effectively cleaned. Additionally, displacing and vibrating the rack from its resting position prevents seals between the endoscope and the contact point of the rack from forming.

The piston 344 is driven by a driving system 360, such as a motor drive system or a pneumatic or hydraulic drive system. In a pneumatic system, a gas supply, such as an air tank, pump, compressor or the like (not shown) supplies air to a rearward portion 362 of the cavity 340, located rearward of the cylindrical portion of the piston, through a first air inlet line 364. As the air enters (activation), the tip of the piston shaft 352 is driven forward and outward from the housing. The piston may be returned to its deactivated position by allowing the air to flow out of the rear chamber 362. More preferably, the piston is withdrawn back into the cylinder, i.e., is deactivated, by forcing air via a second air inlet line 366 into a forward portion 368 of the cavity 340. During the activation portion of the cycle, air may be displaced from the forward portion 368 of the cavity via line 366 and, similarly, during deactivation, air may be displaced from the rearward portion 362 of the cavity via line 364.

For example, air is pulsed into the housing every 1–20 seconds, preferably, about every 10 seconds. Activating the cylinder at regular short intervals may set the rack in "continuous" motion, i.e., the rack is basically constantly moving and does not remain at rest (in the vertical position) for significant periods of time. Studies comparing the pulsed rack with a stationary rack have found a reduction in microbial count as the instruments are decontaminated, particularly when cleaned with relatively low levels of antimicrobial agents.

The housing 338 and piston 344 reside in the chamber 12 and thus are both within the sterile fluid pathway. To avoid harboring and growth of microorganisms within the housing and possible recontamination of the sterilized endoscopes after the sterilization portion of the cycle it is desirable to seal the cavity from the chamber 12. A sealing member 370, such as a gasket, is positioned between the housing and the wall and held in place by the screws 346. A second sealing member 372 is received in a groove 374, in the opening bore 342.

The activation system can be activated in any cycle or phase of cleaning and decontamination. Preferably, the system is activated during each of the cleaning, sterilization, and rinsing cycles. Moving the rack during each of the cycles allows for all areas of the endoscope to be effectively rinsed, cleaned, and sterilized.

In a typical decontamination cycle, items to be decontaminated are first inserted into the cabinet 10 through the opening 14, with the door 18 open, as shown in FIG. 2. The endoscope B to be cleaned is mounted on the rack 21 and inserted into the chamber 12 with other items to be cleaned and decontaminated. The tubes 180 are connected with their respective endoscope inlet ports 186 and connection ports to connect the endoscope internal passages with the fluid lines. The biopsy forceps are loaded on the rack 21. One or more endoscope valves may be inserted in respective valve reprocessors. The leak detector 204 is connected with the endoscope venting connector port. A fresh cup 44 of concentrated decontaminant and other components is inserted into the well 30 and a restraining member or lid 384 positioned over the cup.

Once all the items are properly positioned and fluid lines connected, the door 18 is brought into the closed position and locked.

Figure 15A:
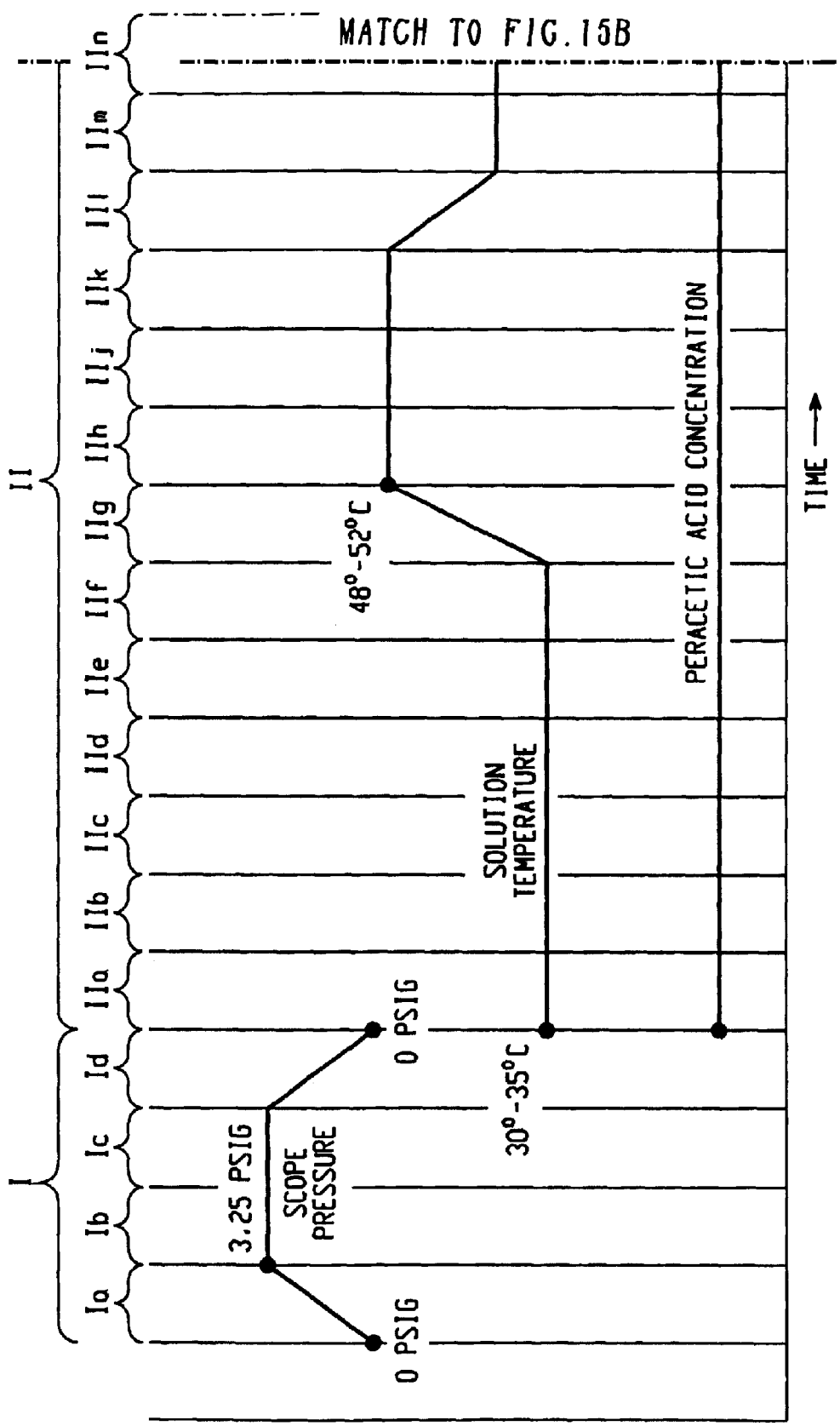
FIGS. 15A and 15B is a plot showing endoscope pressure, fluid temperature, and peracetic acid concentration with time for a washing and microbial decontamination cycle in the processor of FIG. 1.
Figure 15B:
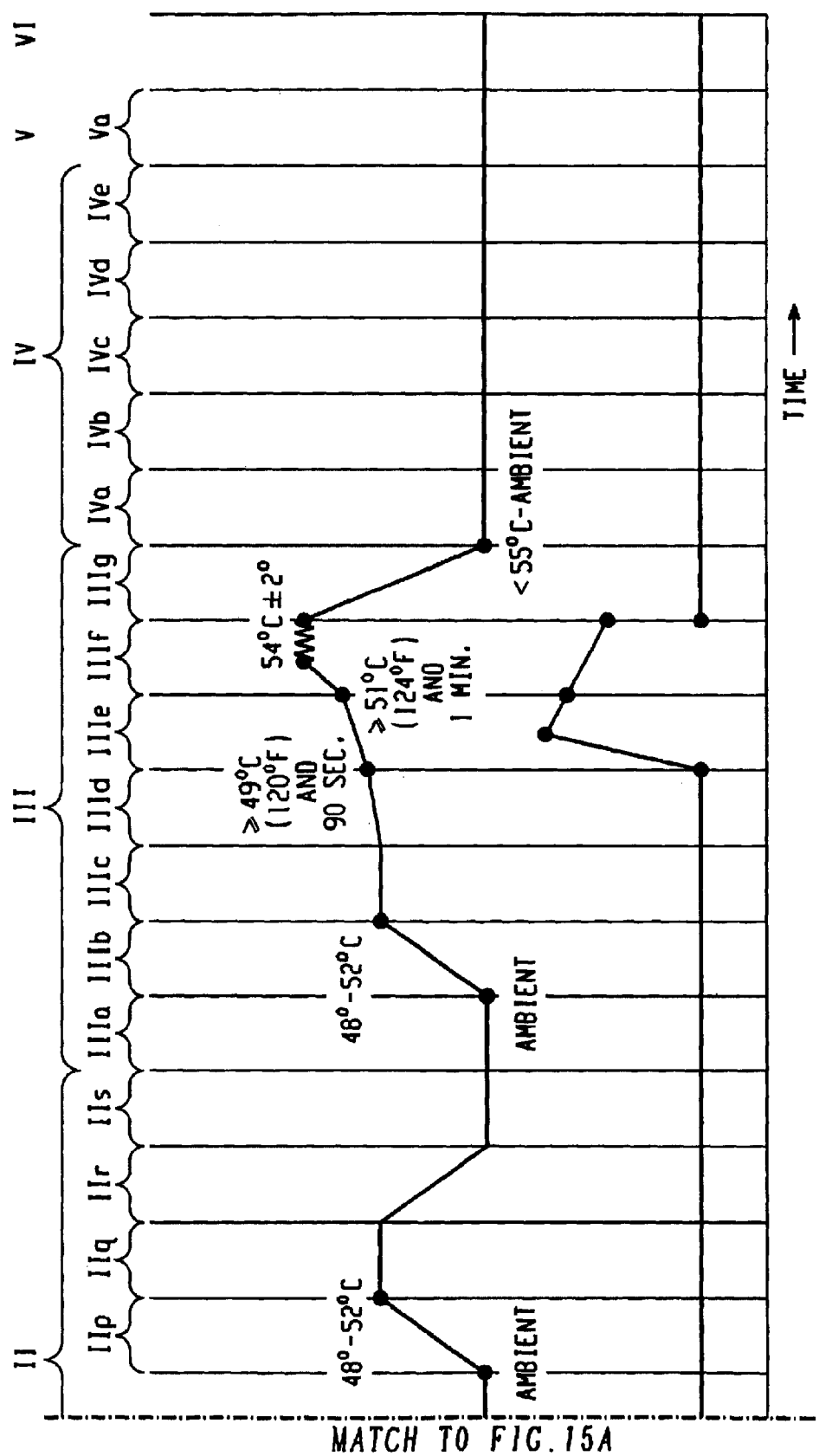

With reference to FIG. 3 and also to FIG. 15, the entire process, including door locking, leak testing, washing, microbial decontamination, and rinsing steps, is fully automated. There is no need for an operator to contact the items until all of the steps are complete. As shown in FIG. 15, a typical cycle includes five phases, a leak testing phase I, a prerinse and washing phase II, a microbial decontamination phase III, a rinse phase IV, and a drying phase V, which are carried out in sequence.

In phase I, the control system 80 signals the leak tester 204 to check the endoscope for leaks. If all is satisfactory, phase II begins. The control system can be programmed to skip this step, if, for example, the device does not have an internal passage to be tested.

In phase II, the items are preferably subjected to a prerinse operation, stages IIb–IId, in which the items are sprayed externally and flushed internally with warm (about 30–35° C.) water for about one minute to remove the bulk of gross debris. The temperature of the water is selected to prevent protein denaturation. Denatured proteins adhere to surfaces and are difficult to remove. Accordingly, the water is kept below 40° C. to prevent this denaturation. All of the soil and other debris which is rinsed off the device is captured in a filter 386, such as a backwashable drain strainer, and is not recirculated through the fluid distribution system. During drain portions of the cycle, the filter is flushed to remove debris.

After about 1 minute of prerinsing, the control system signals a drain valve 388 in the fluid line 60 to open and the rinse water is flushed from the system A to the drain.

In stage IIe, the endoscope is flushed with air. Specifically, the control system 80 signals a valve 390 in an air line 392 to open and supply microbe-free compressed air to the system to remove excess water from the items. The air is preferably passed through a HEPA microbe removal filter 394 before entering the system.

In stage IIg, the computer control 80 signals the valve 52 in the water inlet line 42 to open, allowing water to circulate through the well and the fluid lines 60. In stage IIh, the heater 64 heats the water to a suitable temperature for cleaning. The temperature selected is within the range of temperature to which the device may be subjected, while providing effective cleaning. For endoscopes which have a maximum rating of 60° C., that are being cleaned with a detergent based washing solution, a preferred washing solution temperature is from about 48–52° C. If an enzymatic cleaner is to be used, the temperature selected will also depend on the stability and operating temperatures of the enzymes employed.

In stage IIj, the computer control system 80 signals the opening member 48 to open the cleaner compartment 45 of the cup. The cleaner concentrate mixes with the water to form the washing solution and is delivered by the pump 22 under pressure to the nozzles 102, 104, 106, 108, 110 and endoscope connection ports 150, 152, 154, 156 in stage IIk. The nozzles spray the washing solution over the outer surfaces of the items while the connection ports deliver the solution to the internal passages, thereby cleaning inner and outer surfaces simultaneously. Sprayed washing solution, which drips off the items, is collected in the sump 22. The pump 22 returns the collected solution from the sump to the fluid supply line 60, preferably after first passing at least a part of the collected solution through the well 30 to ensure complete mixing of the cleaner in the solution. A sensor 398, such as a conductivity detector detects whether there is concentrated cleaner in the washing solution, for example, by measuring the conductivity of the circulating washing solution. The rack activation system 330 may be operated during this stage.

The washing solution removes soil from the items, leaving them clean, but not necessarily free of viable microorganisms. The spray jets are particularly effective in this physical cleaning stage.

If the instruments to be cleaned have been left for a relatively long period between use and processing (greater than about an hour), it is preferable to use an enzymatic soak prior to, or in place of, the washing phase. This helps to loosen the blood and other proteins, which gradually harden and become difficult to remove. The enzymatic soak preferably lasts from about 10 minutes to about an hour. In the soak, the enzymatic washing solution is circulated slowly through the system. An additional compartment may be provided in the cup 44, if enzymatic cleaning as well as detergent washing steps are to be used. The control system 80 is programmable to provide for an enzymatic soak in place of, or in addition to, a normal washing step.

Once the washing solution has been circulated through the system for sufficient time to remove the soil from the endoscope and other items, the control system signals drain valve 388 in the fluid line 60 to open and the washing solution is flushed from the processor A to the drain. Optionally, in stage III, the water inlet valve 52 is opened to allow additional fresh water into the system to flush the washing solution from the fluid lines 60,24 and the well 30. The drain valve 388 is then closed. Another air flush/drying step is preferably carried out as stage IIm to remove excess water from the items. In stage IIn–s, an additional hot water rinse and dry is optionally carried out.

Optionally, the devices are manually cleaned, rather than being washed in the processor A. In such cases, the operator programs the control system 80 to skip the washing and optionally the rinsing steps IIj–s. A cup 44 which lacks the compartment holding the concentrated cleaning agent is used.

In stage IIIa–c, the control system 80 opens the valve 52 for a short period to allow more water into the processor and signals the heater to heat the water. Once sufficient water has entered the system for carrying out the decontaminant part of the cycle, the controller 80 signals the valve 52 to close. The control system 80 signals the cup cutter 48 to open the second compartment 46 of the cup 44, containing the pretreatment components (stage IIId). These are released into the fluid lines and are circulated through the processor as a pretreatment solution. The pump 22 circulates the pretreatment solution so that the pretreatment chemicals are distributed throughout the processor A and over the items to be microbially decontaminated, prior to admission of the decontaminant. The pretreatment components buffer the water in the fluid lines to an appropriate pH (typically pH 5–9) for effective decontamination. The corrosion inhibitors present coat the parts of the processor to be exposed to the decontaminant solution and the surfaces of items to be decontaminated with traces of inhibitors to provide resistance to the corrosive effects of the decontaminant.

Although the pretreatment components may be alternatively included in one or other of the cleaner and decontaminant compartments 45, 47 their effectiveness is lessened. By releasing corrosion inhibitors before the microbial decontaminant, the inhibitors are assured time to develop protective barriers around the parts before the parts are contacted by the decontaminant. The buffers modify the pH of the fluid circulating in the system to near neutral with a preferred pH of 6–8. Until the buffer has circulated throughout the system, the microbial decontaminant is not fully effective. Additionally, such agents may degrade the microbial decontaminant during storage. Accordingly, it is preferable to provide a separate compartment 46 for the pretreatment components and allow them to circulate through the system for a period of time before introducing the decontaminant.

After a preselected period of circulation, the controller 80 signals the cutter assembly to open the third compartment 47 (stage IIIe). The decontaminant then mixes with the pretreatment components in the fluid lines 60, 24 and is sprayed through the nozzles 102, 104, 106, 108, 110 and delivered to the endoscope connection ports 150, 152, 154, 156, so that the decontaminant solution flows over the exterior surfaces and through the internal passages of the items to be decontaminated (stage IIIf). The nozzles pulse the decontaminant fluid in a preselected sequence to ensure full coverage of the spray. A decontaminant sensor 402 in fluid communication with one of the fluid flow lines 60, 24 optionally detects the concentration of the decontaminant in the circulating fluid to ensure that a threshold concentration for effective decontamination is provided. The control system controls the heater so that an optimum temperature for decontamination is maintained. Once again, the optimum temperature is dependent on the maximum rating for the device being decontaminated, and also on the effective temperature for the decontaminant. For peracetic acid sterilization of endoscopes rated to 60° C., a preferred minimum temperature of about 48–55° C., more preferably, about 50° C., for the circulating decontaminant solution is maintained. During this stage, the controller controls operation of the rack activation system 330 to ensure that the points of contact between the endoscope and the rack are changed at intervals throughout the microbial decontamination stage.

The chamber is maintained under a slight positive pressure during decontamination to minimize ingress of outside air into the chamber. Air exits the chamber through vents (not shown), which provide a tortuous pathway to minimize air ingress.

After a period of circulation of the decontaminant solution sufficient to effect decontamination of the items (typically about 10–15 minutes for complete sterilization, more preferably, about 12 minutes; 2–5 minutes for high level disinfection, more preferably, about 3 minutes), the drain valve 388 in the processor A is opened and the decontaminant solution flushed from the processor A to the drain (stage IIIg). The circulation period is optionally adjusted in accordance with monitored decontaminant levels during the cycle.

The rinse phase IV then begins. The drain valve 388 is kept open and the control system opens a valve 404 to allow a source 406 of sterile rinse water to supply sterile water to the fluid lines 60 for rinsing the decontaminated items without risk of recontamination of the decontaminated items. The source of sterile water preferably comprises a water heater 408 which heats incoming tap water to a sufficient temperature to destroy microorganisms (preferably about 150° C.) in the water, and a heat exchanger 410, which transfers excess heat from the sterilized water to the incoming tap water (FIG. 3). The water heater helps remove salts from the incoming water which could otherwise deposit on the washed and microbially decontaminated instruments. The water produced by the sterile water generator 406 is thus of high purity. The sterile water generator 406 provides water on demand, eliminating the need to store large quantities of sterile water. The rinse phase may include several fill and blow off stages (IVa–e).

Alternatively, the water inlet valve 52 is opened once more to provide rinse water for rinsing the decontaminated items again. During the rinse stage, the rack activation system 330 may be operated to help ensure that the antimicrobial fluid is rinsed from all the exterior surfaces of the endoscope.

The system A has a fill of about 9 liters. A typical cycle includes 6 fills, for a total fluid requirement of 54 liters, as follows;

1) for pre-rinsing,
2) for forming the washing solution,
3) rinsing the washing solution from the system,
4) for forming the pretreatment and decontaminant solution, and
5) and 6) for sterile rinsing.

After the rinse water has been discharged to the drain, the control system 80 signals the valve 390 in air line 392 to open and supply microbe-free air to the system to blow accumulated water out of and off of the decontaminated items. The air line is connected with the manifold 26 so that the air flows through the nozzles and connection ports, drying the interior and exterior surfaces of the endoscopes and other items. The regulator valves 168, 170, 172, and 174 ensure that the internal passages of the endoscope B are not pressurized beyond their recommended pressure ratings.

Optionally, an alcohol flush is used in addition to, or in place of the last of the rinse steps IVa–e. In this case, a source of alcohol 420 supplies the alcohol to the chamber to remove excess water from the device B. Remaining alcohol quickly evaporates from the device. FIG. 3 shows the source of alcohol connected with the connection ports 150, 152, 154, via a pump 422 for delivering the alcohol to the internal lumens of the device, although it is also contemplated that the alcohol may be supplied to the nozzles also, for drying the exterior of the device.

Optionally, the device may be kept in the chamber for an extended period, such as overnight, to increase water removal. Or the air used to flush the device may be heated to increase evaporation and water removal.

At the end of the cycle (stage VI), the controller 80 signals the cutter assembly 48 to retract from the cup 44 to its starting position and the door locking mechanism to disengage.

Because the steps of leak testing, washing, decontaminating, rinsing, and air drying are carried out automatically and sequentially within the chamber, the entire reprocessing cycle can be carried out in a relatively short period of time, typically 30 to 40 minutes for full sterilization, 20–30 minutes for high level decontamination. The endoscopes are thus ready for reuse in a much shorter time than conventional cleaning and decontamination processes, in which an operator carries out the reprocessing steps using a number of separate pieces of equipment.

The decontaminated items are removed from the decontamination chamber 12 for immediate use or transferred to sterile pouches and stored until needed. The rack 21 can be used to transport the endoscope B to a storage cabinet or to a surgery. The rack handle is configured for carrying the rack and for supporting the rack in the storage cabinet. Thus, the endoscope need not be touched until it is to be used in a surgical procedure, minimizing the potential for contamination.

Optionally, the device B is enclosed in a sterile pouch before removal from the chamber, to minimize airborne re-contamination prior to reuse. For example, the device may be wrapped in a bag, within the chamber, prior to opening of the door. This may be achieved by suitable controls, or manually, for example with a glove box-type of device in which the operator removes the various connectors from the device and wraps the device in the bag using sterile gloves (not shown) which extend into the chamber.

In an alternative embodiment, the chamber 12 acts as a sterile pouch and is hermetically sealed and disconnected from the rest of the processor A and transported to the site at which the decontaminated items are to be used.

Suitable concentrated cleaning agents are low foaming detergents or enzymatic cleaners, with a pH close to neutral (preferably pH 6–8), to minimize corrosion of metal components.

Various antimicrobial agents may be utilized for the decontaminant. In a preferred embodiment, the decontaminant is a solution of peracetic acid. However, it is also contemplated using other liquid or powdered decontaminants or reagents which react in a common solvent to generate peracetic acid, chlorine, hydrogen peroxide, hypochlorous acid, hypochlorite, or other strong oxidants which have biocidal effects. Aldehydes, such as glutaraldehyde, may be used, but the decontaminant solution should be collected after use and properly treated, rather than disposed of via the drain.

Preferably, the pretreatment agent includes a buffer and a corrosion inhibitor. One preferred buffering system includes a combination of monosodium phosphate, disodium phosphate and hexametaphosphates. Such a buffering system also provides anticorrosion properties. Wetting agents and other corrosion inhibitors may alternatively be used. Preferred copper and brass corrosion inhibitors include azoles, benzoates, other five-membered ring compounds, benzotriazoles, tolyltriazoles, mercaptobenzothiazole, and the like. Other anti-corrosive compounds include phosphates, molybdates, chromates, dichromates, tungstates, vanadates, borates, and combinations thereof.

The corrosion inhibitory agents are selected in accordance with the nature of the materials in the items being cleaned and/or decontaminated with the decontaminant. Corrosion inhibitors which protect against corrosion of aluminum and steel, including stainless steel, include phosphates, sulfates, chromates, dichromates, borates, molybdates, vanadates, and tungstates. Some additional aluminum corrosion inhibitors include 8-hydroxyquinoline and ortho-phenylphenol.

More specifically, phosphates are preferred for inhibiting stainless steel corrosion. Preferred phosphates include, but are not limited to, monosodium phosphate (MSP), disodium phosphate (DSP), sodium tripolyphosphate (TSP), sodium hexametaphosphate (HMP), and sodium sulfate either alone or in combination. Preferred borates include sodium metaborate ($NaBO_2$).

Copper and brass corrosion inhibitors include triazoles, azoles, benzoates, tolyltriazoles, dimercapto-thiadiazoles, and other five-membered ring compounds. Particularly preferred copper and brass corrosion inhibitors include sodium salts of benzotriazole and tolyltriazole which are preferred due to their stability in the presence of strong oxidizing compounds. Mercaptobenzothiazole can also be utilized but is apt to be oxidized or destabilized by strong oxidizers. Salicylic acid is an example of an acceptable benzoate corrosion inhibitor.

In hard water, phosphate buffers and corrosion inhibitors tend to cause calcium and magnesium salts present in the hard water to precipitate and coat the instruments being decontaminated and/or cleaned and also leaves deposits on parts of the system. In such cases, a sequestering agent appropriate to prevent precipitation such as sodium hexametaphosphate (HMP), or trisodium nitrolotriacetic acid (NTA $Na_3$) is preferably provided. Because sodium hexametaphosphate is also a corrosion inhibitor, it serves a dual purpose, both as a corrosion inhibitor and as a sequestering agent. Other sequestering agents include sodium polyacrylates. Of course, if soft or deionized water is utilized, the sequestering agent may be eliminated. However, to ensure universal applicability with any water that might be utilized, the presence of a sequestering agent is preferred.

Surface energy reducing agent (surfactants/wetting agents) are preferably agents to increase penetration into crevices of items being treated. This is particularly important when cleaning and decontaminating complex medical instruments which may contain microbial contaminants in crevices, joints, and lumens. Surface energy reducing agents usable in accordance with the present invention include anionic, cationic, nonionic, amphoteric, and/or zwitterionic surfactants. Specific classes of surfactants which are useful include anionic and nonionic surfactants or combinations thereof. Examples of nonionic surfactants usable in the present invention include surfactants such as fatty alcohol polyglycol ethers, nonylphenoxypoly (ethyleneoxy) ethanol, and ethoxylated polyoxypropylene. Specific examples include Genapol UD-50 ™, Igepal™, Fluowet™, and Pegal™. The surfactants set forth above may be used alone or in combination with each other.

Amounts of the corrosion inhibitors and surfactants to be used in the peracetic acid solution will vary depending upon the type of agent being added and whether or not one or more agents are added.

Without intending to limit the scope of the invention, the following examples illustrate the effectiveness of the pulsed rack.

EXAMPLES

Example 1

Endoscopes were inoculated with a soil, placed on a hanging rack, and then subjected to a cleaning cycle, as previously described herein. Two trials were conducted to test cleaning efficacy of a cleaning system utilizing a stationary rack, and a cleaning system utilizing moveable/swinging rack in accordance with the present invention.

Figure 16:
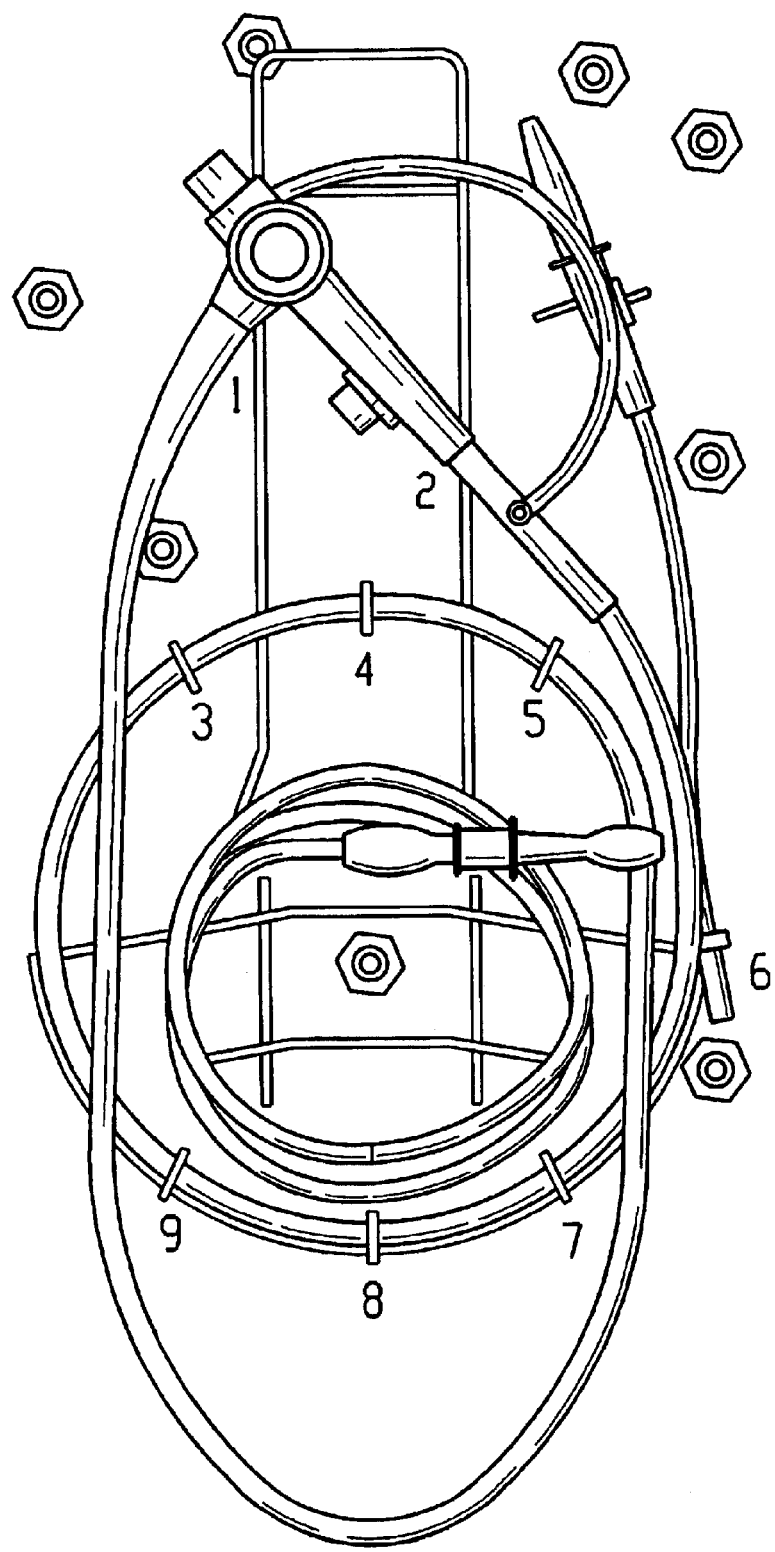
FIG. 16 shows an endoscope coiled on a rack with sampling positions marked.

The test procedure was as follows. With reference to FIG. 16, endoscopes were inoculated with a soil and placed on a rack. Nine selected surface sites, numbered 1–9 on FIG. 16, were inoculated with a standard Edinburg™ soil, comprising egg white and blood, and around $10^6$ staphylococcus bacteria to produce about $10^4$ microorganisms per site. The surface sites were selected to be sites making contact with a portion of the rack. The endoscopes were placed on the rack in the manner displayed in FIG. 16. Endoscopes were subjected to an antimicrobial cleaning cycle similar to that described. However, the peracetic acid concentration was lower than that normally used. Here, peracetic acid having a concentration of about 1000 ppm was used during the sterilization phase to emphasize worst case concentration or MEC (MEC=minimum effective concentration).

Upon completion of the cleaning cycle, each of the nine sites were harvested and plated to determine if any bacteria were present on the endoscope. The sites were swabbed with a sterile growth medium, and the swabs cultured in a test tube for 3–7 days.

In Trial 1, a piston system was not employed and the rack remained stationary during the entire cleaning process. In Trial 2 the rack and endoscope were placed in a cleaning chamber utilizing a piston activated swinging rack system in accordance with the present invention. The piston was activated every 10 seconds by pulsing air into the cylinder, as previously described herein.

Table 1 displays the results from the cleaning trials. A (+) indicates a positive test, i.e., a positive test for bacterial growth.

| Site | Trial 1 | | Trial 2 | |
| --- | --- | --- | --- | --- |
| | Colonies | Bacterial Growth | Colonies | Bacterial Growth |
| 1 | 0 | − | 11 | + |
| 2 | 0 | − | 0 | − |
| 3 | 206 | + | 0 | − |
| 4 | 29 | + | 0 | − |
| 5 | 0 | − | 0 | − |
| 6 | 6 | − | 0 | − |
| 7 | 0 | − | 0 | − |
| 8 | 12 | + | 0 | − |
| 9 | 0 | − | 0 | − |

Table 1 shows that endoscopes, specifically contact sites between the endoscope and the hanging rack are effectively cleaned a swinging or moving rack is employed. Only the test handle (site 1) showed a small bacteria count, even at the low peracetic acid concentrations used in the test.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A system for microbially decontaminating a device, the system including:
    a cabinet which defines an interior chamber for receiving the device;
    spray nozzles, disposed within the chamber, for spraying a decontaminant fluid over an external surface of the device;
    a rack which supports the device, the rack hanging within the chamber; and
    an activation system which displaces at least a portion of the rack for changing points of contact between the device and the support.

2. A system for microbially decontaminating a device, the system comprising:
    a cabinet which defines an interior chamber for receiving the device;
    spray nozzles, disposed within the chamber, for spraying a decontaminant fluid over an external surface of the device;
    a support which supports the device within the chamber, the support being supported adjacent an upper end for pivotal movement;
    an activation system which displaces at least a portion of the support for changing points of contact between the device and the support, the activation system including a means for periodically pivoting the support.

3. The system of claim 2, wherein the support includes a rack and further including a hanger in the chamber on which the rack is removably and pivotally hung.

4. The system of claim 2, wherein the support is supported on at least one hook on a wall of the chamber.

5. A system for microbially decontaminating a device, the system comprising:
    a cabinet which defines an interior chamber for receiving the device;
    spray nozzles, disposed within the chamber, for spraying a decontaminant fluid over an external surface of the device;

a support which supports the device within the chamber; and an activation system which displaces at least a portion of the support for changing points of contact between the device and the support, the activation system including a piston assembly.

6. The system of claim 5, further including:

a pneumatic system which provides motive power to the piston assembly.

7. The system of claim 5, wherein the piston assembly includes:

a piston body portion;

a shaft extending from the piston body portion and intermittently engaging the support when the piston assembly is activated; and a piston cylinder in which the piston body portion is slidably received.

8. A system for microbially decontaminating a device, the system comprising:

a cabinet which defines an interior chamber for receiving the device, the nozzles and the device being positioned within the chamber such that the external surface of the device is impacted with a spray from at least one nozzle at an angle of no more than 45 degrees from perpendicular to the external surface;

a support which supports the device within the chamber;

spray nozzles, disposed within the chamber, for spraying a decontaminant fluid over an external surface of the device;

an activation system which changes points of contact between the device and the support.

9. A system for microbially decontaminating a device with flexible portions, the system comprising:

a cabinet which defines an interior chamber for receiving the device;

spray nozzles, disposed within the chamber, for spraying a decontaminant fluid over the device;

a support which supports the device within the chamber, the support including pegs which position the device such that the flexible portions of the device are bent into an arc with a minimum radius of no less than 15 centimeters; and an activation system which displaces at least a portion of the support changing points of contact between the device and the support.

10. A system for microbially decontaminating a device, the system comprising:

a chamber for receiving the device;

spray nozzles, disposed within the chamber, for spraying a decontaminant fluid over an external surface of the device;

a support which supports the device within the chamber;

an activation system which displaces at least a portion of the support for changing points of contact between the device and the support; and a clip which releasably couples a tip portion of the device to one of the support and another portion of the device, to keep the tip portion securely positioned.

11. The system of claim 10, wherein the clip includes at least one upper finger and at least one lower finger, the fingers each contacting the device at a ridge to minimize contact between the clip and the device.

12. A system for cleaning and microbially decontaminating endoscopes, the system comprising:

a cabinet defining a vertically elongated chamber having rear and side walls and a front door;

spray nozzles mounted on at least the rear and side walls of the chamber for spraying liquid cleaning and microbially decontaminating solutions;

a hanger on the chamber rear wall;

a rack configured to support a coiled endoscope, the rack being pivotally and removably hung on the hanger; and a reciprocating drive having a drive member extending from the chamber rear wall adjacent the rack such that as the drive member reciprocates it engages and pushes the rack to pivot on the hanger and disengages from the rack to permit the liquid cleaning and decontaminating solutions to contact engaging surfaces of the rack and the drive member.

13. A method of microbially decontaminating a device comprising:

(a) mounting the device on a support;

(b) spraying a microbial decontaminant solution over the device to microbially decontaminate the exterior surfaces of the device; and (c) during at least step (b), agitating the support to change points of contact between the device and the support.

14. The method of claim 13, wherein the step of agitating the support includes:

striking the support at intervals such that the support pivots around a pivot point.

15. The method of claim 14, wherein the support is struck at least once every 10 seconds.

16. The method of claim 13, wherein the step of agitating the support includes:

at intervals of time, driving a piston between first and second positions such that a shaft connected with the piston strikes the support.

17. The method of claim 16, wherein the step of driving the piston includes pneumatically driving the piston.

18. The method of claim 13, further including:

supporting the support in a chamber such that the support is free to pivot when agitated.

19. The method of claim 13, wherein the step of spraying a microbial decontaminant solution includes alternating spraying from different directions to change points of contact between the support and the device.

20. The method of claim 13, wherein a first set of the spray nozzles sprays the decontaminant solution for a first period of time and then a second set of the spray nozzles sprays the decontaminant solution for a second period of time.

* * * * *